(12) United States Patent
Adachi et al.

(10) Patent No.: US 7,883,466 B2
(45) Date of Patent: Feb. 8, 2011

(54) ULTRASONIC PROBE APPARATUS AND ULTRASONIC DIAGNOSTIC APPARATUS

(75) Inventors: Hideo Adachi, Iruma (JP); Yoshiyjki Okuno, Fussa (JP); Akiko Mizunuma, Hachioji (JP); Katsuhiro Wakabayashi, Hachioji (JP); Takuya Imahashi, Kawasaki (JP); Yukihiko Sawada, Tokorozawa (JP); Masayoshi Omura, Saitama (JP); Etsuko Omura, legal representative, Saitama (JP); Kozaburo Suzuki, Hachioji (JP); Shuji Otani, Oume (JP); Naomi Shimoda, Fukushima (JP); Miyuki Murakami, Hino (JP); Kiyoshi Nemoto, Hino (JP)

(73) Assignee: Olympus Corporation, Tokyo (JP)

( * ) Notice: Subject to any disclaimer, the term of this patent is extended or adjusted under 35 U.S.C. 154(b) by 1094 days.

(21) Appl. No.: 11/636,678

(22) Filed: Dec. 8, 2006

(65) Prior Publication Data

US 2007/0083119 A1    Apr. 12, 2007

Related U.S. Application Data

(63) Continuation of application No. PCT/JP2005/010591, filed on Jun. 9, 2005.

(30) Foreign Application Priority Data

Jun. 11, 2004  (JP)  ............................. 2004-174565
Jun. 14, 2004  (JP)  ............................. 2004-176039

(51) Int. Cl.
  *A61B 8/00*  (2006.01)
(52) U.S. Cl. ...................... 600/437; 600/407; 600/443
(58) Field of Classification Search ......... 600/407–461; 606/128
  See application file for complete search history.

(56) References Cited

U.S. PATENT DOCUMENTS 6,592,525 B2    7/2003   Miller et al.

(Continued)

FOREIGN PATENT DOCUMENTS

JP    59-115771    7/1984

(Continued)

OTHER PUBLICATIONS

Jin X.C. et al., "Micromachined Capacitive Ultrasonic Immersion Transducer for Medical Imaging" *Proceedings of the 20th Annual International Conference of the IEEE Engineering in Medicine and Biology Society* 20(2):779-782 (1998).

(Continued)

*Primary Examiner*—Brian Casler
*Assistant Examiner*—Nasir Shahrestani
(74) *Attorney, Agent, or Firm*—Scully, Scott, Murphy & Presser, P.C.

(57) ABSTRACT

An ultrasonic probe apparatus which applies a RF pulse signal with a DC bias signal superimposed thereon to c-MUTs and transmits/receives an ultrasound wave is configured such that a transmission control system includes bias regulators which regulate the voltage value of the DC bias signal, a reception control system has a plurality of different frequency band pass filtering characteristics including at least those for a low pass and high pass and a frequency band pass filtering processing section which can select at least one frequency band pass filtering characteristic from those frequency band pass filtering characteristics. The apparatus controls voltage settings of the bias regulators in conjunction with the selection of frequency band pass filtering characteristics of the frequency band pass filtering processing section.

20 Claims, 12 Drawing Sheets

U.S. PATENT DOCUMENTS

| | | |
|---|---|---|
| 6,605,043 B1 | 8/2003 | Dreschel et al. |
| 6,645,145 B1 | 11/2003 | Dreschel et al. |
| 6,773,401 B1 | 8/2004 | Dreschel et al. |
| 6,795,374 B2 * | 9/2004 | Barnes et al. ............... 367/138 |
| 2003/0149363 A1 | 8/2003 | Dreschel et al. |

FOREIGN PATENT DOCUMENTS

| | | |
|---|---|---|
| JP | 11-226010 | 8/1999 |
| JP | 2002-530145 | 9/2002 |
| JP | 2003-164456 | 6/2003 |
| JP | 2004-503312 | 2/2004 |
| JP | 2004-503313 | 2/2004 |
| WO | WO 00/30543 | 6/2000 |
| WO | PCT/EP2001/006479 | 6/2001 |
| WO | PCT/EP2001/006868 | 6/2001 |

OTHER PUBLICATIONS

Ladabaum I. et al., "Surface Micromachined Capacitive Ultrasonic Transducers", *IEEE Transactions on Ultrasonics, Ferroelectrics, and Frequency Control 45* (3):678-690 (1998).

* cited by examiner

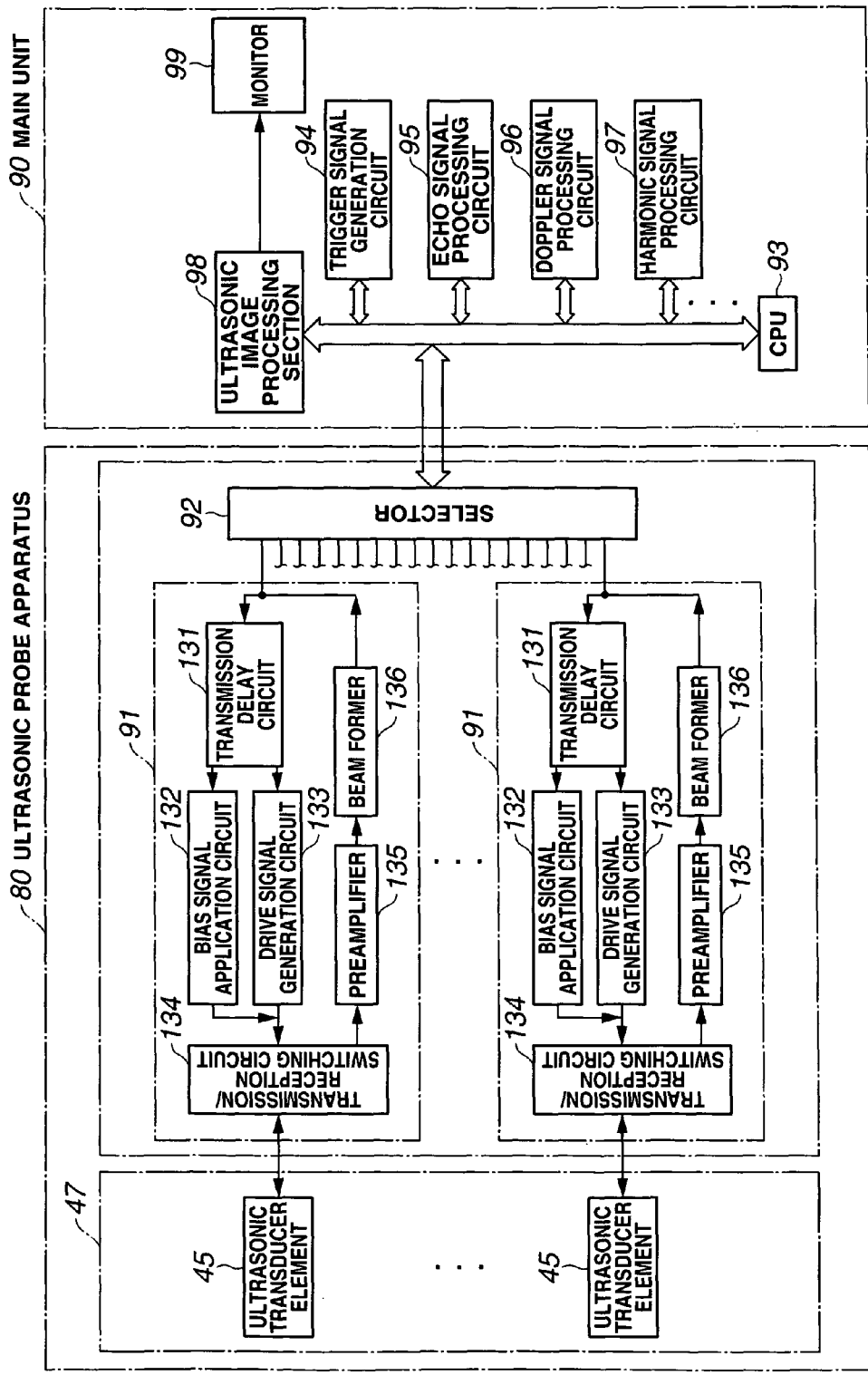

ULTRASONIC PROBE APPARATUS AND ULTRASONIC DIAGNOSTIC APPARATUS

CROSS REFERENCE TO RELATED APPLICATION

This application is a continuation application of PCT/JP2005/010591 filed on Jun. 9, 2005 and claims benefit of Japanese Applications No. 2004-174565 filed in Japan on Jun. 11, 2004 and No. 2004-176039 filed in Japan on Jun. 14, 2004, the entire contents of each of which are incorporated herein by their reference.

BACKGROUND OF THE INVENTION

1. Field of the Invention

The present invention relates to an ultrasonic probe apparatus and an ultrasonic diagnostic apparatus which perform ultrasonic observation and diagnosis using a capacitive micromachined ultrasonic transducer (hereinafter abbreviated as "c-MUT") which is pivotably supported at an end of an insertion section inserted into the body cavity.

2. Description of the Related Art

Prime importance is being placed on an ultrasonic diagnostic technology whereby for example, forceps of an endoscope are inserted, an ultrasonic transducer mounting part is caused to stick out at an end thereof, make contact with body tissues, for example, a stomach wall and thereby visualize information on the depth of the stomach wall, for example, a layered structure of the mucous membrane by means of ultrasound waves with high resolution.

On the other hand, a harmonic imaging diagnosis using a harmonic signal is becoming a standard diagnostic modality in recent years because it can obtain a clear diagnostic image which could not be obtained by a conventional B mode diagnosis.

The harmonic imaging diagnosis can be classified under two categories; (1) a tissue harmonic imaging method of separating, when an ultrasound wave is propagating in a body, harmonics superimposing on a fundamental ultrasound wave under the nonlinear influence of the body tissue using various methods and constructing an image using this signal and (2) a contrast harmonic imaging method of injecting contrast medium bubbles into the body, receiving harmonics produced at the moment bubbles burst or resonate through irradiation of transmission ultrasound waves, separating harmonics superimposed on fundamental ultrasound waves using various methods and constructing an image using this signal.

All these methods are proven to have such a high S/N that cannot be obtained from a conventional B mode tomogram and be able to obtain a diagnostic image with high resolution, thus contributing to improvement of the accuracy of medical diagnostics.

As for an ultrasonic transducer which is used for a conventional extracorporeal harmonic imaging diagnostic apparatus, for example, an identical transmission/reception dual-function ultrasonic transducer has been used for both transmission of fundamental waves and reception of harmonics. It is also possible to adopt a structure whereby an echo of an ultrasonic pulse reflected from a body tissue is received through an ultrasonic transducer provided apart from the one for transmission.

Since the signal level of a harmonic signal is much smaller than that of a fundamental wave, it is necessary to efficiently remove a fundamental wave component involved in deterioration of a harmonic image. For this purpose, a publicly known harmonic component (especially second-order harmonic component) extraction technology is used.

As an ultrasonic transducer, a c-MUT obtained by forming on a silicon semiconductor substrate using silicon micromachine technology is becoming a focus of attention in addition to a conventional piezoelectric type ultrasonic transducer.

As examples of prior arts of the c-MUT, National Publication of International Patent Application No. 2004-503312 and National Publication of International Patent Application No. 2004-503313 disclose the following. That is, each of a plurality of c-MUTs has a charged diaphragm and this charged diaphragm faces an oppositely charged substrate so as to produce a capacitance in between. This diaphragm is attracted to the substrate with bias charge. This substrate has a central part which rises toward the center of the diaphragm so that the charge of a cell has a maximum density in the center of the movement of the diaphragm. For a harmonic operation, a drive pulse applied to the cell is distorted beforehand in view of a nonlinear operation of the apparatus to reduce mixing of a distortion component of a transmission signal into a harmonic frequency band. A transmission ultrasound wave into which this distortion component has been mixed contains a high frequency component from the beginning, and therefore it is impossible to distinguish whether the received high frequency component detected is the high frequency component mixed from the beginning or the high frequency component is originated from the body. Since the c-MUT cell can be worked on through a conventional semiconductor process, it can be united with an auxiliary transducer circuit such as a bias charge regulator. The c-MUT cell can be further processed through micro stereo lithography, and therefore the cell can be formed using a variety of polymers and other substances.

The c-MUT generally requires not only a RF pulse signal but also a DC bias voltage to generate an ultrasound wave during both transmission and reception. That is, the c-MUT generates a signal composed of a DC bias voltage superimposed on a RF pulse signal, applies the signal to the c-MUT and thereby transmits/receives ultrasound waves.

Using a harmonic imaging technology requires an ultrasonic transducer having a wideband characteristic, and since the c-MUT has a wideband characteristic, it is suitable for a harmonic imaging diagnosis.

SUMMARY OF THE INVENTION

The ultrasonic probe apparatus according to the present invention is an ultrasonic probe apparatus which applies a RF pulse signal with a DC bias signal superimposed thereon to a c-MUT and transmits/receives an ultrasound wave, including bias adjustment means provided for a transmission control system for adjusting a voltage value of the DC bias signal and frequency band pass filtering processing means provided for a reception control system, which has a plurality of different frequency band pass filtering characteristics including at least those for a low pass filtering and a high pass filtering and can select any one of the frequency band pass filtering characteristics.

In the present invention, the plurality of different frequency band pass filtering characteristics are three frequency band pass filtering characteristics of a low frequency band pass filtering characteristic, a high frequency band pass filtering characteristic and an intermediate frequency band pass filtering characteristic which is intermediate between the low frequency band pass filtering characteristic and the high frequency band pass filtering characteristic.

It is preferable to further include means for controlling a voltage setting of the bias adjustment means in conjunction with a frequency band pass filtering characteristic selection of the frequency band pass filtering processing means.

For example, the frequency band pass filtering processing means is set to a low frequency band pass filtering characteristic when the DC bias voltage is set to be low and the frequency band pass filtering processing means is set to a high frequency band pass filtering characteristic when the DC bias voltage is set to be high.

Since the present applicant has experimentally discovered that changing a DC bias voltage causes the peak frequency (frequency at which the amplitude level becomes a maximum) of a transmission ultrasound wave to change, the present invention uses this result. That is, when a DC bias voltage is set to be low by a transmission control system and a frequency band pass filtering processing means is set to a low frequency band pass filtering characteristic by the reception control system, an ultrasound wave of a low frequency component is sent and received (corresponding to FIG. 1A), and therefore it is possible to observe the depth of a body tissue while keeping sensitivity. On the other hand, when the DC bias voltage is set to be high by the transmission control system and the frequency band pass filtering processing means is set to a high frequency band pass filtering characteristic by the reception control system, an ultrasound wave of a high frequency component is sent and received (corresponding to FIG. 1C), and therefore it is possible to perform an observation with increased resolution in a near acoustic field.

Furthermore, in the present invention, the c-MUT has an array structure made up of a plurality of transducer elements, and comprises means for selecting transmission transducer elements from the plurality of array transducer element groups, drive means for applying a drive signal to each of the selected transmission transducer elements, transmission delay means for performing scanning with a transmission ultrasonic beam, means for selecting reception transducer elements from the plurality of array transducer element groups, amplification means for amplifying a reception signal from each of the selected reception transducer elements, frequency band pass filtering processing means for performing frequency band pass filtering processing, analog/digital signal conversion means, beam synthesis means for synthesizing a plurality of reception signals, image constructing means and image display means.

The drive signal from the drive means is preferably a pulse signal composed of a DC pulse signal superimposed on a RF pulse signal.

According to the present invention, the DC bias voltage is not applied all the time, but a drive pulse signal composed of the DC pulse voltage superimposed on a RF pulse signal is applied to the c-MUT with consideration for a reduction of an operating effective voltage.

In the present invention, the DC pulse signal draws a curve similar to a Gaussian function or a COS function on a rising edge and a falling edge.

In this way, the DC pulse signal draws a curve similar to a Gaussian function or a COS function on a rising edge and/or a falling edge, and can thereby provide a gentle inclination, prevent a precipitously high voltage from adding to the c-MUT and prevent the capacitative transducer from deteriorating, preventing the life thereof from becoming short.

In the present invention, the RF pulse signal is a spike-shaped pulse.

A sine pulse wave is normally used as the RF pulse signal, but a spike pulse may be used and superimposed on the DC pulse signal instead. By adjusting the DC bias component in this case, too, it is possible to obtain an amplitude characteristic dependent on the DC bias voltage, spectral characteristic and amplitude characteristic at each peak of the low frequency component and the high frequency component as in the case where a sine wave shaped pulse wave is used.

Furthermore, in the present invention, the voltage setting of the bias adjustment means and the frequency band characteristic selection of the frequency band pass filtering processing means are successively changed, ultrasonic reception data obtained for each change is temporarily stored in storage means, the data are synthesized and image constructing means constructs an ultrasonic diagnostic image signal.

In the voltage setting of the bias adjustment means, the frequency band pass filtering processing means selects a low frequency band pass filtering characteristic when selecting a low voltage setting and the frequency band pass filtering processing means selects a high frequency band pass filtering characteristic when setting a high voltage.

Furthermore, in the voltage setting of the bias adjustment means, the means for selecting a transmission transducer element selects a transmission transducer element disposed in the vicinity of the periphery of an ultrasonic transmission opening when selecting a low voltage setting and the means for selecting a transmission transducer element selects a transmission transducer element disposed in the vicinity of a central part of the ultrasonic transmission opening when selecting a high voltage setting.

According to the present invention, the DC bias voltage is decreased so that an ultrasound wave of the low frequency component is transmitted from the transducer element on the circumference of the opening of the c-MUT and the DC bias voltage is controlled to be high so that the ultrasound wave of the high frequency component is transmitted from the transducer element of the central part of the opening. It is possible to maintain sensitivity in the deep part at a low frequency, increase resolution in a near acoustic field at a high frequency and obtain a sound field with high sensitivity (that is, high sound pressure) up to the deep part synthesizing both over the entire opening.

In the above described configurations, it is possible to realize an ultrasonic probe apparatus using a c-MUT, operating on a low operating effective voltage, usable in the body cavity, having a high degree of depth reaching capability with high sensitivity, applicable to a harmonic imaging diagnosis and with little deterioration of the transducer.

The ultrasonic probe apparatus of the present invention is a capacitative ultrasonic probe apparatus including drive signal generation means for applying a RF pulse signal with a DC bias voltage superimposed thereon to an c-MUT, an ultrasound wave being transmitted/received through the application of the drive signal, wherein means for supplying the DC bias voltage comprises means for outputting a DC pulse signal at a predetermined period and controlling pulse generation timing, pulse width and pulse voltage of the DC pulse signal.

According to the present invention, instead of applying a DC bias voltage to the capacitative ultrasonic probe apparatus all the time, a drive pulse with a DC pulse voltage superimposed on a RF pulse signal is applied thereto. This reduces an operating effective voltage and is also convenient from the standpoint of safety management.

Furthermore, in the ultrasonic probe apparatus of the present invention, the drive signal generation means generates a double pulse signal combining a first superimposed pulse signal composed of a RF pulse signal superimposed on a DC pulse signal with one polarity and a second superimposed pulse signal composed of a RF pulse signal having the same shape as that of the RF pulse signal used to form the first superimposed pulse signal superimposed on a DC pulse signal having a polarity opposite to the polarity of the DC pulse signal used to form the first superimposed pulse signal in such a way that the two signals appear one after another with a predetermined time interval.

The present invention uses a technique whereby a double pulse combining a pulse with a RF pulse signal superimposed on a positive DC bias signal and a pulse with a RF pulse signal superimposed on a negative DC bias signal is used as a drive pulse, a preceding pulse of a reception echo signal of the ultrasonic pulse (this, too, is a double pulse) is temporarily stored in a memory, and both pulses are added up at the same time as a following pulse is generated to thereby separate a harmonic component and construct an image, and this technique can be used for a harmonic imaging diagnosis.

Furthermore, the ultrasonic probe apparatus of the present invention includes a c-MUT assembled using a micromachine technology, drive control means constructed substantially integral therewith and signal transmission means for exchanging signals.

According to the present invention, it is possible to reduce the size of the apparatus and use the apparatus in the body cavity.

Furthermore, according to the ultrasonic diagnostic apparatus of the present invention, the ultrasonic probe apparatus includes a c-MUT assembled using a micromachine technology, drive control means constructed substantially integral therewith and signal transmission means for exchanging signals, and the ultrasonic diagnostic apparatus is constructed of this ultrasonic probe apparatus and a main apparatus which processes an output signal from the ultrasonic probe apparatus, constructs an image signal and displays an ultrasonic diagnostic image of the interior of the body cavity. The ultrasonic probe apparatus is, for example, a radial scanning array type transducer which performs scanning with an ultrasonic beam around the insertion axis in the body cavity.

According to the present invention, it is possible to realize an ultrasonic diagnostic apparatus using a c-MUT, operating on a low operating effective voltage, usable in the body cavity and also applicable to a harmonic imaging diagnosis.

In the above described configurations, it is possible to realize an ultrasonic probe apparatus and an ultrasonic diagnostic apparatus using a c-MUT, operating on a low operating effective voltage, usable in the body cavity and also applicable to a harmonic imaging diagnosis.

BRIEF DESCRIPTION OF THE DRAWINGS

FIG. 19 is a block diagram showing the configuration of an ultrasonic diagnostic apparatus according to a fourth embodiment of the present invention.

DETAILED DESCRIPTION OF THE EMBODIMENTS

With reference now to the attached drawings, embodiments of the present invention will be explained below.

First Embodiment

Figure 1A:
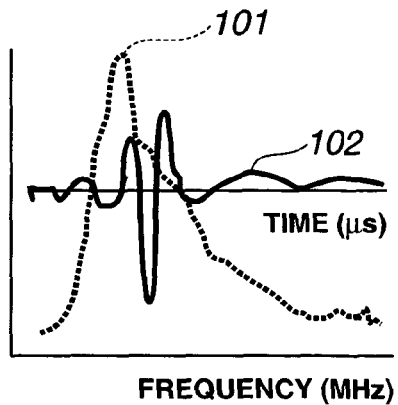
FIG. 1A illustrates an amplitude level characteristic on the time axis of an ultrasonic pulse transmitted when a transmission DC bias voltage applied to a c-MUT is set to a low voltage area and a spectral characteristic thereof.
Figure 1B:
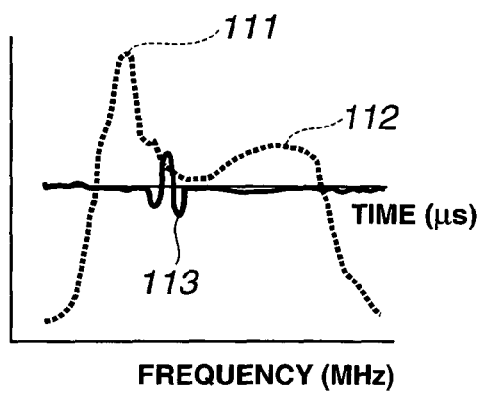
FIG. 1B illustrates an amplitude level characteristic on the time axis of an ultrasonic pulse transmitted when a transmission DC bias voltage applied to a c-MUT is set to a medium voltage area and a spectral characteristic thereof.
Figure 1C:
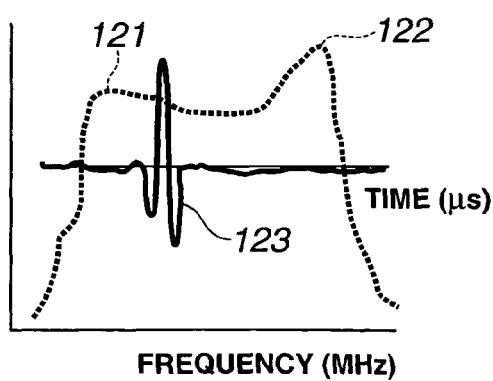
FIG. 1C illustrates an amplitude level characteristic on the time axis of an ultrasonic pulse transmitted when a transmission DC bias voltage applied to a c-MUT is set to a high voltage area and a spectral characteristic thereof.

FIGS. 1A to 1C illustrate time domain (solid line) and frequency domain (dotted line) characteristics respectively of transmitted ultrasonic pulse in the case of varying dc bias level. Time domain characteristics (solid line) of transmitted ultrasonic pulse is a variation in the amplitude level (shown by solid line) on the time axis of an ultrasonic pulse transmitted when a transmission DC bias voltage applied to a c-MUT is changed from low to medium and high and a frequency characteristic (spectrum, shown by dotted line) on the frequency axis obtained by applying a Fourier transform to a real-time waveform thereof. Here, these are measured values when the transmission DC bias voltage is changed. The present applicant has experimentally confirmed that reception is possible even when the reception DC bias voltage is 0.

Figure 2:
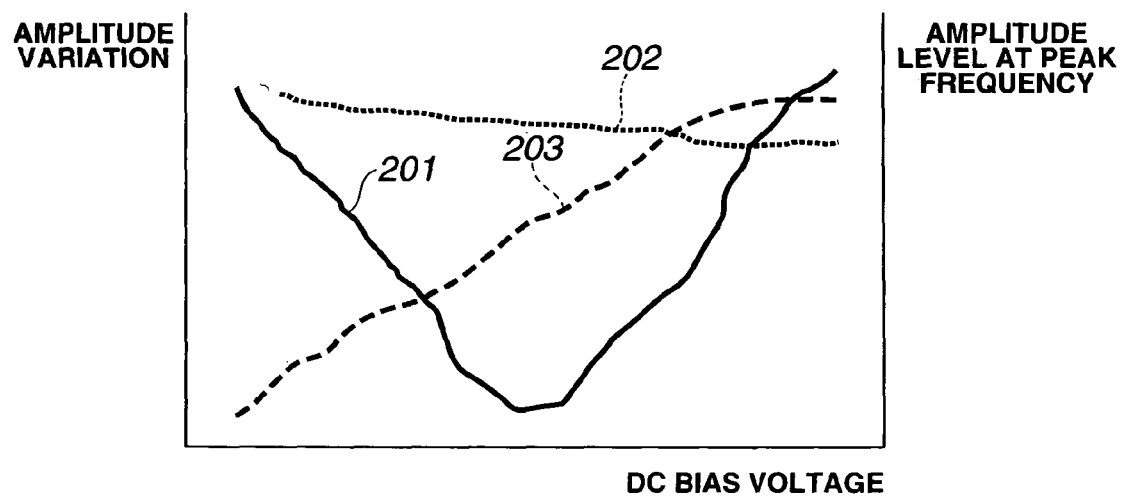
FIG. 2 illustrates an amplitude characteristic versus a variation in a DC bias voltage and an amplitude characteristic at each peak frequency in a low frequency component and a high frequency component created based on FIGS. 1A to 1C.

FIG. 2 illustrates a variation of the peak level of the amplitude in a real-time waveform and a variation of the amplitude level at each peak frequency (frequency at which the amplitude level becomes a maximum) of the low frequency component and the high frequency component when the DC bias voltage on the horizontal axis is changed.

Figure 3:
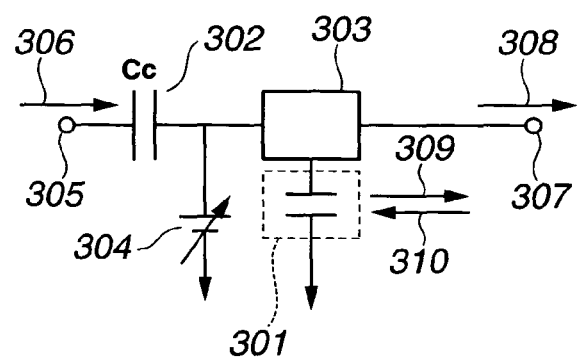
FIG. 3 is a circuit diagram of a measurement circuit when measuring the characteristics in FIGS. 1A to 1C.

FIG. 3 shows a circuit diagram of the measurement circuit when performing measurement shown in FIG. 1A to FIG. 1C.

In FIG. 3, reference numeral 301 denotes a transmission/reception dual-function c-MUT, 302 denotes a DC voltage cut-off capacitor, 303 denotes a transmission/reception switchover switch, 304 denotes a variable DC bias voltage power supply, 305 denotes a drive signal input terminal and 306 denotes a drive signal, 307 denotes a reception signal output terminal, 308 denotes a reception signal, 309 denotes a transmission ultrasonic pulse and 310 denotes a reception ultrasonic pulse. The measurements in FIGS. 1A to 1C are conducted by measuring the signal amplitude of the ultrasonic pulse 309 transmitted when using a RF pulse signal with a predetermined frequency and amplitude as the transmission input signal 306 and changing the DC bias voltage power 304.

FIG. 1A shows a case where an ultrasound wave is transmitted/received with the DC bias voltage set to 0 for both transmission and reception. A solid line 102 indicates the amplitude level with the horizontal axis expressing a time scale, a dotted line 101 indicates the amplitude level with the horizontal axis expressing a frequency. The spectral waveform 101 shown by dotted line is obtained by applying a Fourier transform to the signal waveform 102 on the time axis and converting it to a waveform on the frequency axis. In FIG. 1A, the frequency at which the amplitude of the spectrum waveform 101 becomes a maximum (hereinafter, referred to as a "peak frequency") is relatively low on the frequency axis.

FIG. 1B shows a case where the transmission DC bias voltage is increased a little compared to FIG. 1A and when the transmission DC bias voltage is increased little by little, the waveform amplitude level of the signal on the time axis shown by the solid line becomes a minimum at a certain point. A solid line 113 of FIG. 1B shows a state when the waveform amplitude level of the signal on the time axis becomes a minimum. Even when the waveform amplitude level becomes a minimum, it does not mean that ultrasonic vibration is not obtained at all, but a certain degree of amplitude is obtained. The spectrum is as shown by dotted lines 111 and 112. When the part 111 indicated by dotted line (low frequency part) is compared to the part 101 indicated by dotted line (low frequency part) in FIG. 1A, the part corresponding to 101 remains as the part indicated by reference numeral 111 and at the same time, the level of the high frequency part indicated by reference numeral 112 has increased.

FIG. 1C shows a case where the DC bias voltage is further increased and the peak level at the part (low frequency part) indicated by reference numerals 101 and 111 in FIG. 1A and FIG. 1B relatively decreases and in contrast to this, the part corresponding to the part (high frequency part) 112 shown in FIG. 1B becomes a high level as indicated by reference numeral 122. In this way, when the DC bias voltage is changed, the spectrum indicated with dotted line on the frequency axis changes as shown in FIGS. 1A to 1C. FIG. 2 shows this situation with the DC bias voltage expressed on the horizontal axis.

FIG. 2 shows the DC bias voltage on the horizontal axis and a variation of the amplitude or the amplitude level at a peak frequency on the vertical axis. Solid line 201 shows a variation of peak voltages (amplitudes) of a signal on the time axis such as 102, 113 and 123 in FIGS. 1A to 1C according to the variation of the DC bias voltage. In contrast, the curve shown by thin dotted line 202 shows the amplitude level at peak frequencies 101, 111 and 121 of the low frequency component on the frequency axis in FIGS. 1A to 1C, while the curve shown by thick dotted line 203 shows the amplitude level at peak frequencies 112 and 122 of the high frequency component. In this way, the mode in which the peak level of the low frequency component and the peak level of the high frequency component change varies depending on the DC bias voltage.

Therefore, changing a frequency distribution (spectrum) by changing the DC bias voltage and using a high frequency component for some cases and using a low frequency component in other cases may provide convenience when constructing an ultrasonic image as shown below.

When a low frequency component is output from a transducer element in the vicinity of the periphery of the opening of the ultrasonic transducer and a high frequency component is output from the vicinity of the central part of the opening, sensitivity is kept in a deep part at a low frequency and resolution can be increased in a near acoustic field at a high frequency, and therefore it is possible to obtain a sound field having high sensitivity up to the deep part synthesizing both over the entire opening.

Figure 4:
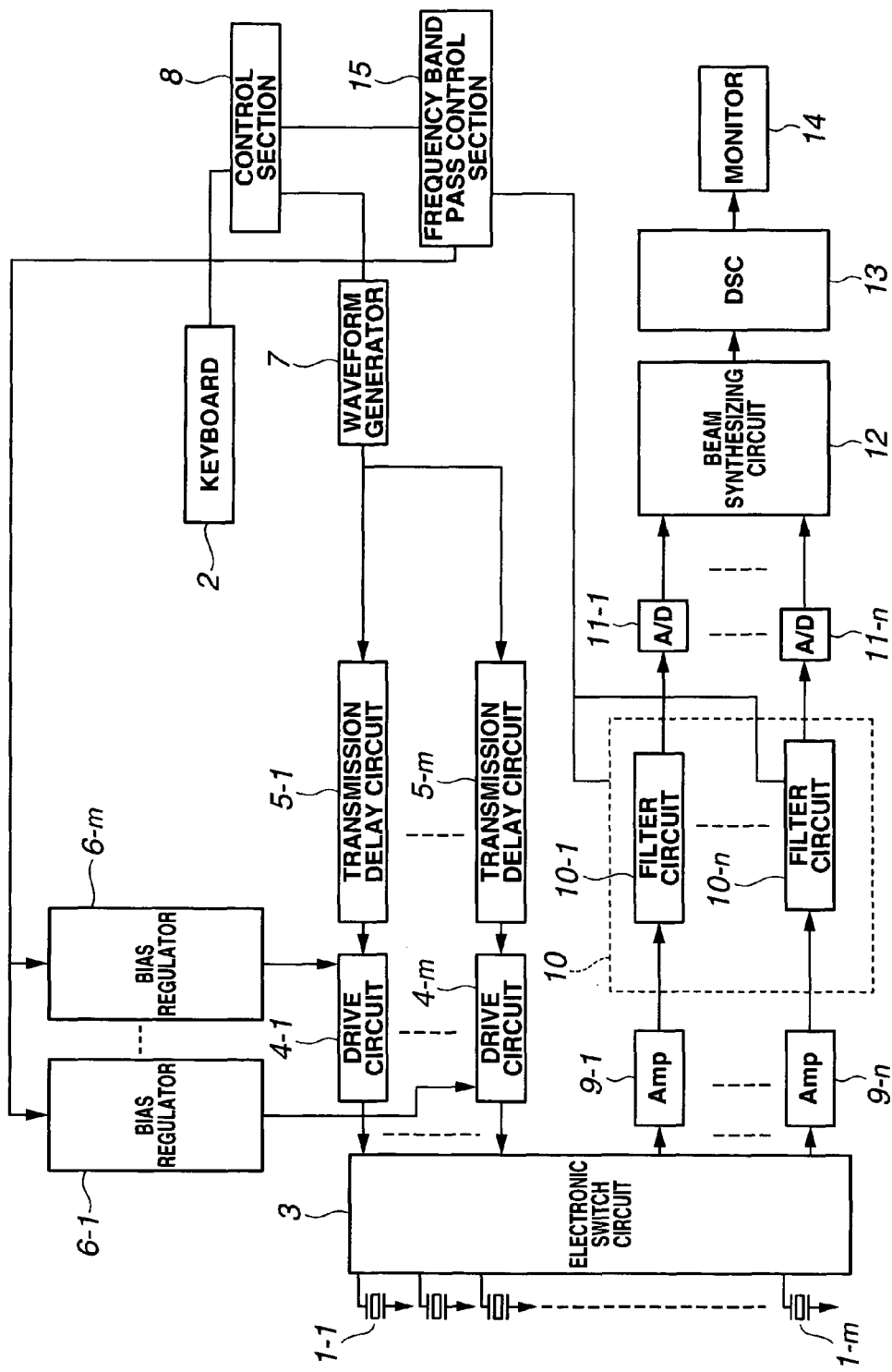
FIG. 4 is a block diagram showing the configuration of an ultrasonic probe apparatus according to a first embodiment of the present invention.

FIG. 4 shows the configuration of an ultrasonic probe apparatus according to the first embodiment of the present invention.

The ultrasonic probe apparatus in FIG. 4 is provided with transducer elements 1-1 to 1-$m$ which constitute a c-MUT, a keyboard 2 as operation means which can select a transmission/reception mode, an electronic switch circuit 3 which switches between transmission and reception, drive circuits 4-1 to 4-$m$ which generate drive signals to drive m transducer elements respectively, transmission delay circuit 5-1 to 5-$m$ which receive RF pulse signals and function as transmission beam formers which generate RF pulse signals given a time difference by performing time delay control on each of the m transducer elements, bias regulators 6-1 to 6-$m$ for generating a low voltage DC bias voltage in such a way as to be regulatable, a waveform generator 7 for generating a low voltage RF pulse signal and supplying it to the above described transmission delay circuit 5-1 to 5-$m$, a control section 8 which can send out a control signal, amplifiers (Amp) 9-1 to 9-$n$ which amplify a reception signal (echo signal), a frequency band pass filtering processing section 10 made up of a plurality of filter circuits 10-1 to 10-$n$ having different frequency band pass filtering characteristics, A/D converters 11-1 to 11-$n$ for converting signals to digital signals, a beam synthesizing circuit 12 which synthesizes a plurality of signals into one signal, a digital scan converter (DSC) 13 as image constructing means for imaging, a monitor 14 as a display device (image display means) and a frequency band pass control section 15.

The drive circuits 4-1 to 4-$m$ have the function of superimposing time delay controlled low voltage RF pulse signals input from the transmission delay circuits 5-1 to 5-$m$ on low voltage DC bias voltages input from the bias regulators 6-1 to 6-$m$, thereby generating low voltage drive signals and then amplifying these signals to generate and output high voltage drive signals. Here, the "low voltage" means a low voltage equal to or less than 10 V, while the "high voltage" means a high voltage of approximately 150 to 200 V.

The keyboard 2, drive circuits 4-1 to 4-$m$, transmission delay circuit 5-1 to 5-$m$, bias regulators 6-1 to 6-$m$, waveform generator 7, control section 8 and frequency band pass control section 15 constitute a transmission control system. Furthermore, the amplifiers 9-1 to 9-$n$, frequency band pass filtering processing section 10, A/D converters 11-1 to 11-$n$, beam synthesizing circuit 12, digital scan converter (DSC) 13 and monitor 14 constitute a reception control system.

As for the relationship between reference characters m and n, 1 to m are used for the transducer elements and the transmission control system circuits, 1 to n are used for the reception control system circuits, and there is a relationship of m≧n. As for the transducer elements 1-1 to 1-m, transmission is performed using all m pieces during transmission and reception is performed using only n of m pieces during reception. Therefore, m circuits are involved in each circuit of a transmission operation during transmission in the transmission control system, while n circuits are involved in a reception operation in each circuit of the reception control system.

The array of c-MUT elements may be an array of the c-MUT elements at the opening of the ultrasonic transducer made up of the transducer elements 1-1 to 1-m or may be an array of the respective ultrasonic transducer elements in the periphery and central part of the opening. The electronic switch circuit 3 is needed to switch between transmission and reception. The drive circuits 4-1 to 4-m supply the high-voltage drive pulse signals with a DC bias voltage added to the RF pulse signals to the same number of transducer elements as the drive circuits 4-1 to 4-m. The electronic switch circuit 3 selects m transducer elements and inputs drive pulse signals from the m drive circuits 4-1 to 4-m in the case of transmission, and selects n transducer elements and outputs reception signals from n transducer elements in the case of reception.

The transmission delay circuit 5-1 to 5-m are means for focusing an ultrasonic beam on a point of an object to be observed and correspond to beam forming for transmission. The beam synthesizing circuit 12 is used for beam forming for reception.

The bias regulators 6-1 to 6-m generate low voltage DC bias voltages in such a way as to be regulatable and the waveform generator 7 is the circuit which generates low voltage RF pulse signals. Low voltage signals are used at the waveform generator 7, bias regulators 6-1 to 6-m and transmission delay circuit 5-1 to 5-m, and the interior of each drive circuit 4-1 to 4-m receives a low voltage signal from the preceding section, adds up the DC bias voltage from the bias regulator 6-1 to 6-m and the RF pulse signal from the transmission delay circuit 5-1 to 5-m in a low voltage condition, amplifies this addition signal and outputs it as a high voltage signal.

As described above, by changing the DC bias voltage, it is possible to change the frequency spectrum of the ultrasound wave, and therefore a DC bias voltage is set at the bias regulators 6-1 to 6-m to specifically generate a spectrum and filtering that matches the spectrum is performed during reception in accordance with the spectrum. When, for example, a DC bias voltage is set to a relatively high value to generate a high frequency component signal, the filter circuits making up the frequency band pass filtering processing section 10 select a high pass filter (HPF) for passing a high frequency area of the reception signal, while when a DC bias voltage is set to a relatively low value to generate a low frequency component signal, the filter circuits making up the frequency band pass filtering processing section 10 select a low pass filter (LPF) for passing a low frequency area of the reception signal. In this way, frequency band pass filtering characteristics of the filter circuits making up the frequency band pass filtering processing section 10 on the receiving side is selected in conjunction with the level of the DC bias voltage. The plurality of signals which have passed through the plurality of filter circuits 10-1 to 10-n making up the frequency band pass filtering processing section 10 are converted to a plurality of digital signals respectively at the A/D converters 11-1 to 11-n, supplied to the beam synthesizing circuit 12 and synthesized into a single signal. The single signal obtained at the beam synthesizing circuit 12 is converted to an image by the digital scan converter (DSC) 13 and then presented, that is, displayed on the monitor 14.

In FIG. 4, the A/D converters 11-1 to 11-n are provided after the frequency band pass filtering processing section 10, but the positions of the A/D converters need not be after the frequency band pass filtering processing section 10. For example, the A/D converters 11-1 to 11-n may be provided after the amplifiers 9-1 to 9-n and the plurality of filter circuits 10-1 to 10-n making up the frequency band pass filtering processing section 10 may be constructed of n digital filter circuits.

Figure 5:
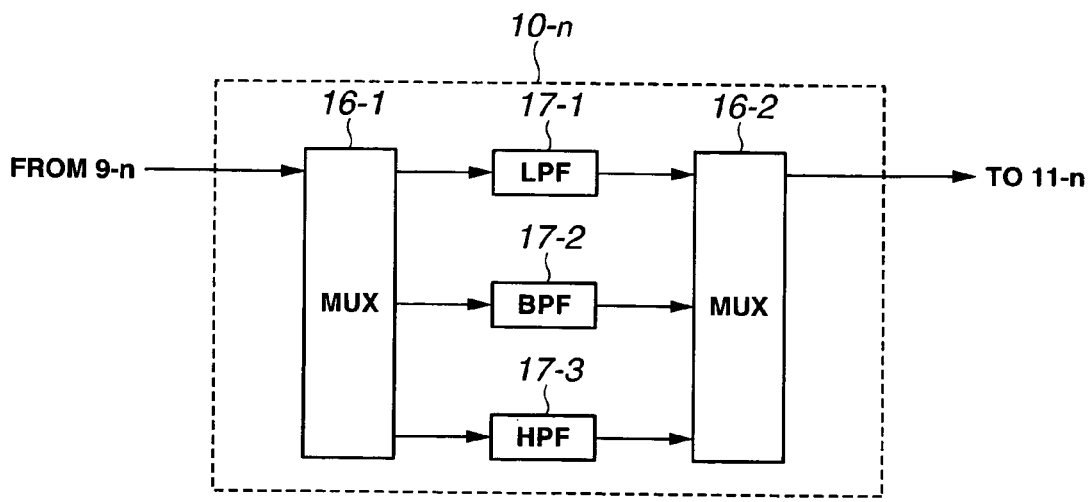
FIG. 5 is a block diagram showing the configuration of the filter circuit in FIG. 4.

The frequency band pass filtering processing section 10 is provided with n filter circuits 10-1 to 10-n, the number of which is equivalent to the number of transducer elements received, and one filter circuit of which, for example, the filter circuit 10-n is constructed as shown in FIG. 5.

The filter circuit 10-n shown in FIG. 5 is constructed of three kinds of filters 17-1, 17-2 and 17-3 of different frequency band passing and multiplexers 16-1 and 16-2 provided on the input side and the output side of these three kinds of filters 17-1, 17-2 and 17-3 respectively to select one of the three kinds of filters 17-1, 17-2 and 17-3. The two multiplexers 16-1 and 16-2 are controlled by a control signal from the frequency band pass control section 15 so as to select the input/output of the same filter at the same time from among the three kinds of filters 17-1, 17-2 and 17-3. The frequency band of the three kinds of filters 17-1, 17-2 and 17-3 may be a low pass filter LPF or high pass filter HPF or band pass filter BPF which is an intermediate frequency band between the low-frequency band and the high-frequency band. For the filter circuit 10-n, a signal from the amplifier 9-n which corresponds to the transducer element 1-n is input to the multiplexer 16-1, passes through any one of the three kinds of filters 17-1, 17-2 and 17-3 selected by the control signal from the frequency band pass control section 15, passes through the multiplexer 16-2 and is output to the following A/D converter 11-n. The same applies to the other filter circuits 10-1 to 10-n−1, too.

The operation of the first embodiment of the present invention will be explained with reference to FIG. 1 to FIG. 5.

The operator selects a mode of transmitting/receiving an ultrasound wave from the keyboard 2 and sends transmission/reception mode information to the control section 8. The control section 8 sends out the above mentioned transmission/reception information to the frequency band pass control section 15 as a control signal. The frequency band pass control section 15 sends out a selection signal for selecting a voltage value of the DC bias signal which corresponds to the above mentioned control signal to the bias regulators 6-1 to 6-m and sends out a selection signal for selecting a filter which corresponds to the above mentioned control signal to the filter circuits 10-1 to 10-n of the frequency band pass filtering processing section 10 at the reception section.

Here, the selection of a transmission/reception mode will be explained. The frequency band of the transmission pulse of the c-MUT can be changed by adjusting the DC bias voltage as described in FIG. 1 and FIG. 2. When a low bias is applied to the transmission signal as shown in FIG. 1A, it is possible to transmit an ultrasound wave having a peak in the low frequency area. By increasing the above described bias voltage, it is possible to transmit an ultrasound wave having a high-frequency component as shown in FIG. 1B. When the bias voltage is further increased, it is possible to transmit an ultrasound wave having a wideband characteristic as shown in FIG. 1C.

Transmission of an ultrasonic signal according to the region to be observed is performed using a variation in the frequency band of the transmission ultrasound waveform caused by a variation in the bias voltage applied to the transmission RF pulse signal.

For example, to observe a region located in a relatively deep part, the bias voltages of the bias regulators 6-1 to 6-m in FIG. 4 are set so as to have the transmission frequency band of FIG. 1A and the frequency band pass filtering processing section 10 in FIG. 4 selects such a filter that includes a peak in the low-frequency area. Furthermore, in a mode in which priority is given to resolution, the bias voltages of the bias regulators 6-1 to 6-m in FIG. 4 are set so as to have a transmission frequency band in FIG. 1B and the frequency band pass filtering processing section 10 in FIG. 4 selects a filter having a wideband characteristic. When catching harmonics represented by "harmonic", the bias voltages of the bias regulators 6-1 to 6-m are set so as to have the transmission frequency band in FIG. 1C and the frequency band pass filtering processing section 10 in FIG. 4 selects a filter having a frequency band that can extract only the high-frequency component. Here, the case where the same sound beam is processed in a single transmission is explained, but it is also possible to successively switch (change) the above described voltage setting of the bias regulators 6-1 to 6-m in FIG. 4 and frequency band pass filtering characteristic selection of the frequency band pass filtering processing section 10 in FIG. 4 for each transmission in a mode in which the same sound beam is transmitted a plurality of times. For example, it is possible to carry out a first transmission of the same sound beam with the frequency band in FIG. 1A, a second transmission with the frequency band in FIG. 1B and extract only harmonics by differentiating the received data obtained. In these operations, a buffer memory is necessary as storage means for temporarily storing received data obtained in each transmission.

To realize these operations, the filter circuit 10-n in FIG. 5 selects any one filter out of the group of filters 17-1 to 17-3 using the multiplexer (MUX) 16-1 and multiplexer (MUX) 16-2 according to the control signal sent from the frequency band pass control section 15 in FIG. 4 above.

Returning to the explanation in FIG. 4, when the start of transmission/reception is instructed from the keyboard 2, a transmission trigger signal is sent from the control section 8 to the waveform generator 7, a transmission signal (RF pulse signal) is output from the waveform generator 7, the bias regulators 6-1 to 6-m apply the bias voltages set by the above described frequency band pass control section 15 to a transmission signal, the transmission delay circuits 5-1 to 5-m add a delay to the transmission signal whose bias voltage is regulated so as to form an arbitrary focus on a patient, the drive circuits 4-1 to 4-m amplify the signal, the electronic switch circuit 3 switches between the transducer elements to be driven and, for example, the transducer elements 1-1 to 1-m radiate ultrasound waves into the body of the patient. The ultrasound waves reflected from the radiation target are received by the transducer elements 1-1 to 1-n, switched to the reception control system by the electronic switch circuit 3, amplified by the amplifiers 9-1 to 9-n, introduced into the filter circuits 10-1 to 10-n of the frequency band pass filtering processing section 10, pass through a filter of the set frequency band, converted to digital signals by the A/D converters 11-1 to 11-n, synthesized into a beam by the beam synthesizing circuit 12, converted to an image signal by the DSC 13 where an image is built, and the image is displayed on the monitor 14.

In the first embodiment in FIG. 4, through the combination of the bias regulators (6-1 to 6-m) and the frequency band pass filtering processing section 10, when the bias regulators 6-1 to 6-m are indicating a low voltage bias, the frequency band pass filtering processing section 10 selects a filter according to the instruction from the frequency band pass control section 15 so that the LPF operates. In this setting, the electronic switch circuit 3 makes a selection so that a drive voltage is applied to the transducers in the periphery (=periphery area of the opening) of the array of the array transducers, and as for the reception signal, the transmission/reception signal (low frequency component) from the periphery of the opening is also handled. This signal provides a deep penetration diagnostic image signal which penetrates to deep area.

On the other hand, when the bias regulators (6-1 to 6-m) are indicating a high voltage bias, the frequency band pass filtering processing section 10 selects a filter according to the instruction from the frequency band pass control section 15 so that the HPF operates. In this setting, the electronic switch circuit 3 makes a selection so that a drive voltage is applied to the transducer in the central part (=central part of the opening) of the array of the array transducers, and as for the reception signal, the transmission/reception signal (high frequency component) from the central part of the opening is also handled. This signal does not reach a deep part but provides a high resolution diagnostic image in a near acoustic field.

Figure 6:
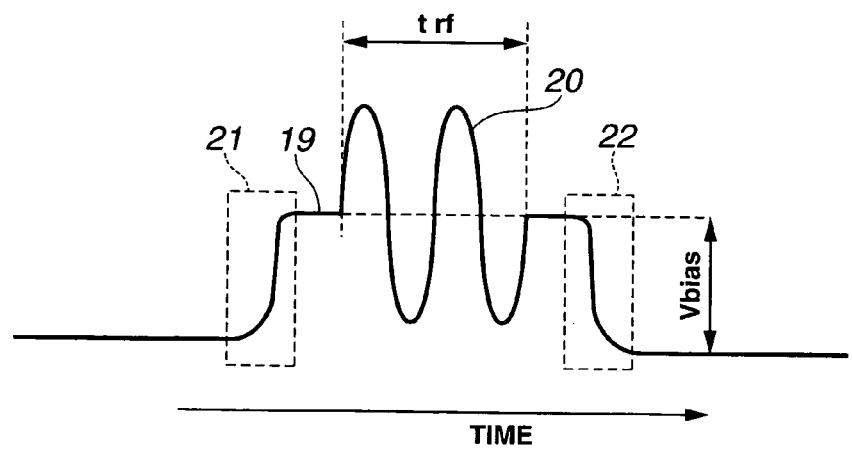
FIG. 6 is a waveform diagram of a drive pulse signal which is applied to the c-MUT from the drive circuit.

FIG. 6 shows a waveform diagram of the drive pulse signal which is applied to the c-MUT from the above described drive circuits 4-1 to 4-m.

The DC bias voltage generation means at each of the drive circuits 4-1 to 4-m generates a DC bias component Vbias as a DC pulse signal 19 having a predetermined pulse width for a predetermined period and with a small effective voltage, and superimposes an original RF pulse signal 20 as a burst wave within the pulse width period of this signal 19. "trf" denotes a RF pulse signal period. In this way, the drive circuits 4-1 to 4-m each generate a drive pulse signal composed of the DC pulse signal 19 having the DC bias component Vbias of a predetermined period superimposed on the RF pulse signal 20, applies the drive pulse signal to the c-MUT and thereby transmits and receives ultrasound wave. In this case, the DC bias voltage generation means may also be provided with the function of generating the DC pulse signal 19 having the DC bias voltage component Vbias of a predetermined period and controlling the pulse generation timing, pulse width and pulse voltage Vbias of the DC pulse signal 19.

By adjusting the DC bias component Vbias in this way, it is possible to obtain the amplitude characteristic which is dependent on the DC bias voltage, spectral characteristic and amplitude characteristic at each peak of the low frequency component and the high frequency component as shown in FIG. 1A to FIG. 1C and FIG. 2.

Furthermore, by blunting a rising edge 21 and a falling edge 22 of the DC pulse signal 19 and transforming them into gentle inclinations and thereby preventing a precipitously high voltage from applying to the ultrasonic transducers, it is possible to prevent the capacitative transducers from deteriorating and prevent the life as the transducers from shortening. More specifically, by causing the DC pulse signal to draw a curve similar to a Gaussian function or COS function on the rising edge 21 and falling edge 22, it is possible to obtain gentle inclinations with tailing.

Note that in FIG. 4, ultrasonic diagnostic images are simply visualized such as the high frequency component and the low frequency component individually in correspondence with the central part and periphery of the opening. In contrast to this, an embodiment whereby both signals of the high frequency component and the low frequency component corresponding to the central part and periphery of the opening are synthesized so as to obtain an ultrasonic diagnostic image which facilitates diagnosis over the entire area (entire opening) will be explained below.

Second Embodiment

Figure 7:
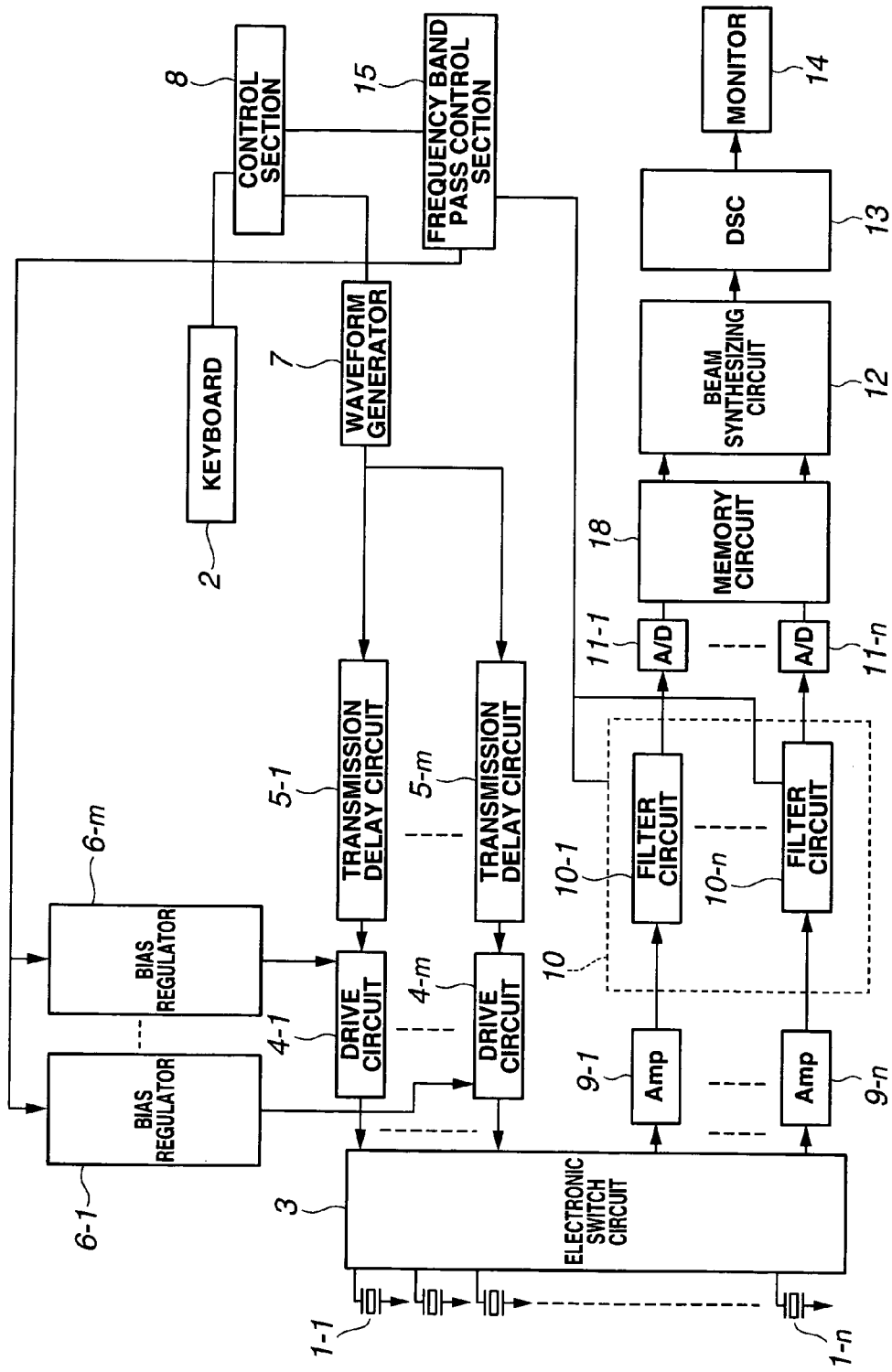
FIG. 7 is a block diagram showing the configuration of an ultrasonic probe apparatus according to a second embodiment of the present invention.

FIG. 7 shows the configuration of an ultrasonic probe apparatus according to a second embodiment of the present invention.

In FIG. 7, what is different from FIG. 4 is that a memory circuit 18 is provided before a beam synthesizing circuit 12. The rest of the configuration is the same as that in FIG. 4.

The memory circuit 18 is provided so that when a high frequency component and a low frequency component corresponding to the central part and periphery of the opening respectively are detected at certain time intervals, if, for example, the high frequency component is extracted first, it can be stored in the memory circuit 18 and when the low frequency component comes later, both components are synthesized and the synthesized signal is supplied to the beam synthesizing circuit 12. The memory circuit 18 is provided as means for causing a temporally preceding signal to temporally coincide with a following signal to link both signals. That is, the high frequency component signal is received and stored in the memory circuit 18 first and when the following low frequency component signal comes, both signals are treated as one set of signals at the same time and subjected to beam forming.

In the second embodiment in FIG. 7 as in the case of the first embodiment in FIG. 4, in the combination of bias regulators (6-1 to 6-$m$) and a frequency band pass filtering processing section 10, when the bias regulators 6-1 to 6-$m$ are indicating a low voltage bias, the frequency band pass filtering processing section 10 selects a filter according to the instruction from a frequency band pass control section 15 so that an LPF operates. In this setting, an electronic switch circuit 3 makes a selection so that a drive voltage is applied to transducers in the periphery (=periphery of the opening) of an array of array transducers, and as for the reception signal, the transmission/reception signal (low frequency component) from the periphery of the opening is also handled. This signal provides a deep penetration diagnostic image signal which penetrates to deep area.

On the other hand, when the bias regulators (6-1 to 6-$m$) are indicating a high-voltage bias, the frequency band pass filtering processing section 10 selects a filter according to the instruction from the frequency band pass control section 15 so that an HPF operates. In this setting, the electronic switch circuit 3 makes a selection so that a drive voltage is applied to the transducer of the central part (=central part of the opening) of the array of the array transducers, and as for the reception signal, the transmission/reception signal (high frequency component) from the central part of the opening is also handled. This signal does not reach a deep part but provides a high resolution diagnostic image in a near acoustic field.

A feature of this second embodiment is that both the high frequency component and the low frequency component signals corresponding to the central part and periphery of the above described opening are synthesized using the memory circuit 18 and it is thereby possible to obtain an ultrasonic diagnostic image which facilitates a diagnosis over the entire area (entire opening). As described above, this is made possible by temporarily storing the preceding reception signal in the memory circuit 18 at the time of synthesis.

Therefore, this second embodiment can be expressed as follows. It is possible to successively change voltage settings of the bias adjustment means and frequency band pass filtering characteristic selections of the frequency band pass filtering processing means, temporarily store ultrasonic reception data obtained for each change in the storage means, synthesize them by the synthetic means, and then construct an ultrasonic diagnostic image signal using the image constructing means.

Figure 8:
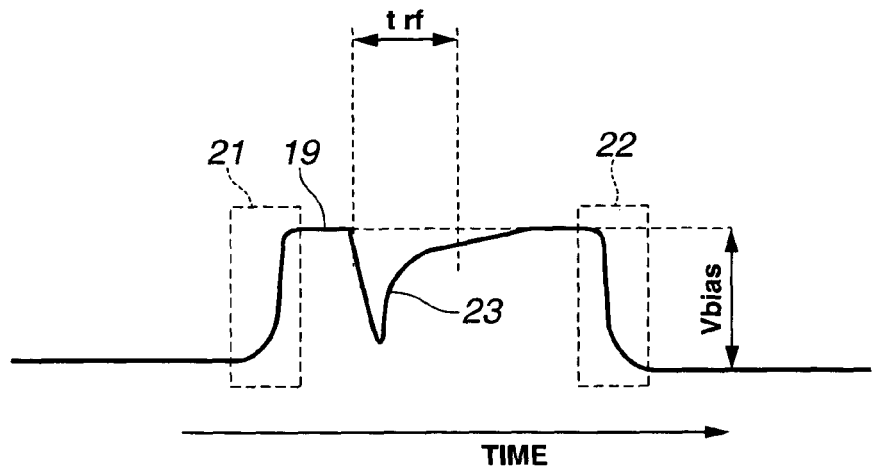
FIG. 8 is waveform diagram showing another example of the drive pulse signal which is applied to the c-MUT from the drive circuit.

In the above described first and second embodiments, a drive signal with a RF pulse signal 20, which is a burst wave, superimposed within the pulse width of the DC pulse signal 19 as shown in FIG. 6 is used as the drive pulse signal. Instead of such a burst wave, it is also possible to superimpose a spike wave 23 on the DC pulse signal 19 as shown in FIG. 8 as the drive pulse signal. Even when the drive pulse signal as shown in FIG. 8 is used, by adjusting a DC bias component Vbias, it is possible to obtain the amplitude characteristic which is dependent on the DC bias voltage, spectral characteristic and amplitude characteristic at each peak of the low frequency component and the high frequency component as shown in FIG. 1A to FIG. 1C and FIG. 2.

Figure 9:
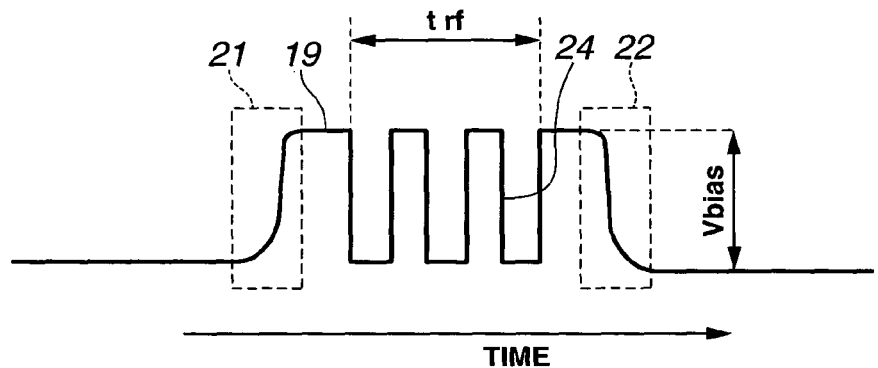
FIG. 9 is a waveform diagram showing a further example of the drive pulse signal which is applied to the c-MUT from the drive circuit.

On the other hand, in the case of a signal composed of a high frequency signal superimposed on the DC pulse signal, the high frequency signal may also be a comb-like square wave 24 as shown in FIG. 9.

In order to obtain a harmonic imaging diagnostic image using the above described harmonic signal extraction technology with the above described circuit in FIG. 4 of the first embodiment and the circuit in FIG. 7 of the second embodiment, a memory circuit is used after the beam synthesizing circuit 12 in FIG. 4 or FIG. 7 to generate one set of fundamental wave double-pulses of an ultrasonic fundamental wave (preceding pulse) and an inverted wave (following pulse) obtained by inverting the polarity thereof at a predetermined interval, send it to a diagnostic target, receive a double-pulse ultrasonic echo signal reflected by and returned from the diagnostic target, and separate and extract only the second-order harmonic component included in the reception signal from the fundamental wave component. This memory circuit to be used for extracting second-order harmonics is preferably disposed after the beam synthesizing circuit 12 in FIG. 4 or FIG. 7. That is, in order to use a harmonic imaging diagnostic technology, it is possible to dispose the memory circuit after the beam synthesizing circuit 12 in FIG. 4 or FIG. 7, temporarily store the preceding pulse of the received double-pulse ultrasonic echo signal in the memory circuit, and when the following pulse comes, add this to the stored preceding pulse, thereby erase the fundamental wave component, and double and extract the second-order harmonic component.

Third Embodiment

Figure 10:
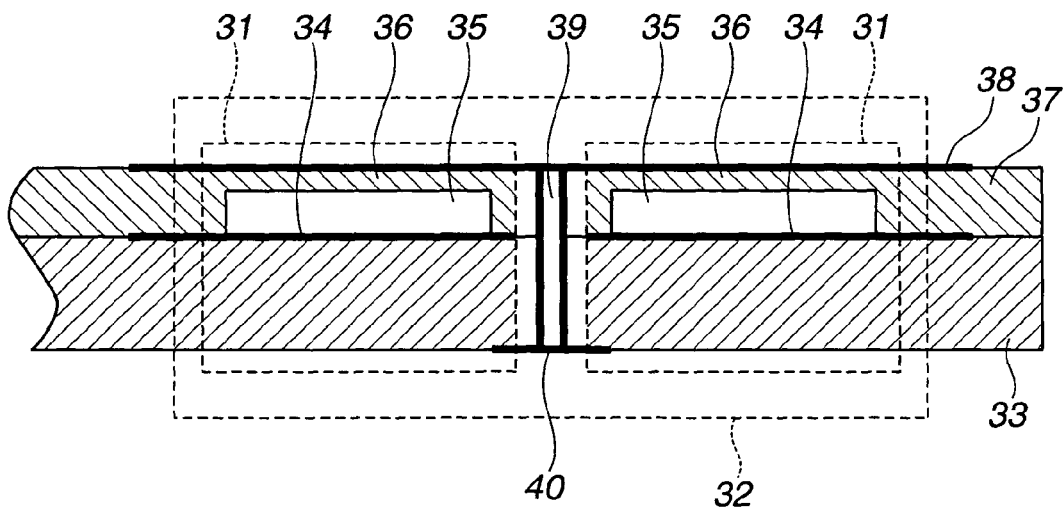
FIG. 10 is a cross-sectional view of a c-MUT which is applied to an ultrasonic probe apparatus according to a third embodiment of the present invention.

FIG. 10 shows a cross-sectional view of an ultrasonic transducer which is applied to an ultrasonic probe apparatus according to a third embodiment of the present invention.

In FIG. 10, one transducer element 32 is constructed of a plurality of (two in the figure) transducer cells 31 and these transducer elements 32 are integrated on a silicon substrate 33 two-dimensionally in the horizontal and depth directions.

First, a silicon substrate 33 is provided and a lower electrode 34 is formed thereon for each cell, a cavity 35 which is an air or vacuum cavity is formed thereon, a vibrating film called a "membrane 36" is formed so as to be supported by a support section 37 and an upper electrode 38 is formed on the membrane 36. The support section 37 is formed using silicon or silicon nitride as a material thereof. The side of the upper electrode 38 from which an ultrasound wave is output is grounded and a conductive connection hole 39 is provided, for example, in the center of the silicon substrate 33 and support section 37 for each element in such a way as to penetrate from the upper electrode 38 to an electrode 40 on the back side of the silicon substrate 33 to bring both electrodes into conduction. Though not shown, since the silicon substrate 33 has very high conductivity, when forming the connection hole 39, the silicon substrate is insulated before forming the conductive film, an insulated area is formed and then the conductive connection hole 39 is formed.

On the other hand, a signal is input and output to/from the lower electrode 34 through an electrode terminal (not shown). That is, the upper electrode 38 is grounded element by element and a signal is also input/output to/from the lower electrode 34 element by element. Note that the neighboring elements are insulated from each other.

Figure 11:
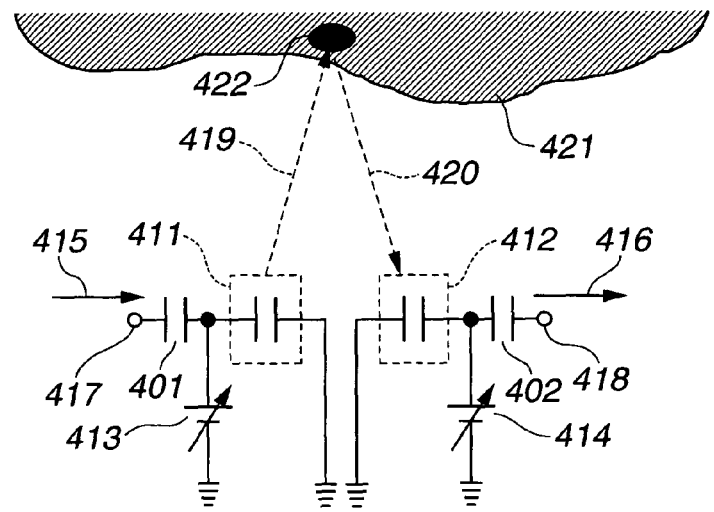
FIG. 11 illustrates the configuration of a transmission/reception isolated type c-MUT.
Figure 12:
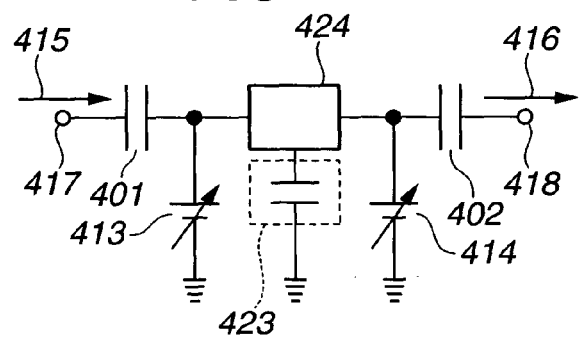
FIG. 12 illustrates the configuration of a transmission/reception dual-function type c-MUT.

There are two ways of use of the ultrasonic transducer; a transmission/reception split type configuration as shown in FIG. 11 whereby a c-MUT for transmission 411 and a c-MUT for reception 412 are formed as independent bodies and a transmission/reception dual-function type configuration as shown in FIG. 12 whereby transmission and reception are carried out by switching one transmission/reception dual-function type c-MUT 423 using a transmission/reception switchover switch 424.

In the transmission/reception split type ultrasonic transducer in FIG. 11, reference numeral 411 denotes the c-MUT for transmission, 412 denotes the c-MUT for reception, 413 denotes a DC bias power supply for transmission, 414 denotes a DC bias power supply for reception, 401 and 402 denote DC blocking capacitors, 415 denotes a RF pulse signal for transmission, 416 denotes a received pulse echo signal, 417 denotes a transmission drive input terminal, 418 denotes a pulse echo signal output terminal, 419 denotes a transmission ultrasound wave, 420 denotes a pulse echo signal, 421 denotes a body tissue and 422 denotes an abnormal tissue.

Of the RF pulse signal 415 for transmission input from the transmission drive input terminal 417, only a high frequency component remains after passing through the DC blocking capacitor 401, is superimposed on the DC bias voltage from the DC bias power for transmission 413 and applied as a drive pulse signal to the c-MUT for transmission 411. With the application of this drive pulse signal, the ultrasound wave 419 is transmitted from the c-MUT for transmission 411, and when, for example, it reaches the abnormal tissue 422 of the body tissue 421, the ultrasound wave 419 is reflected on the tissue, returned as the pulse echo signal 420 and received by the c-MUT for reception 412. The c-MUT for reception 412 is made ready for reception with the DC bias voltage from the DC bias power supply for reception 414 at least at timing of receiving the pulse echo signal 420 and when the capacitance changes with the pulse echo signal 420; the c-MUT for reception 412 outputs the pulse echo signal as an electric signal. The DC blocking capacitor 402 causes only the AC component of the high frequency electric signal to be output from the pulse echo signal output terminal 418. In the above described operation, the pulse echo signal 420 is received while changing the position of the body tissue 421 to which the transmission ultrasound wave 419 is transmitted, and it is thereby possible to recognize the abnormal tissue 422 through a variation in the intensity of the pulse echo signal 420 according to the condition of the body tissue 421 at the position of reflection.

Furthermore, in the transmission/reception dual-function type ultrasonic transducer in FIG. 12, reference numeral 413 denotes a DC bias power supply for transmission, 414 denotes a DC bias power supply for reception, 401 and 402 denote DC blocking capacitors, 415 denotes a RF pulse signal for transmission, 416 denotes a received pulse echo signal, 417 denotes a transmission drive input terminal, 418 denotes a pulse echo signal output terminal, 423 denotes the transmission/reception dual-function c-MUT and 424 denotes the transmission/reception switchover switch.

In the case of FIG. 12, the transmission/reception switchover switch 424 switches between transmission timing at which a drive pulse signal composed of the RF pulse signal for transmission 415 superimposed on the DC bias voltage from the DC bias power supply for transmission 413 is applied to the transmission/reception dual-function c-MUT 423, and reception timing at which the DC bias voltage for reception is applied from the DC bias power supply for reception 414, and in this way transmission and reception are performed using one c-MUT 423 during both transmission and reception.

Figure 13:
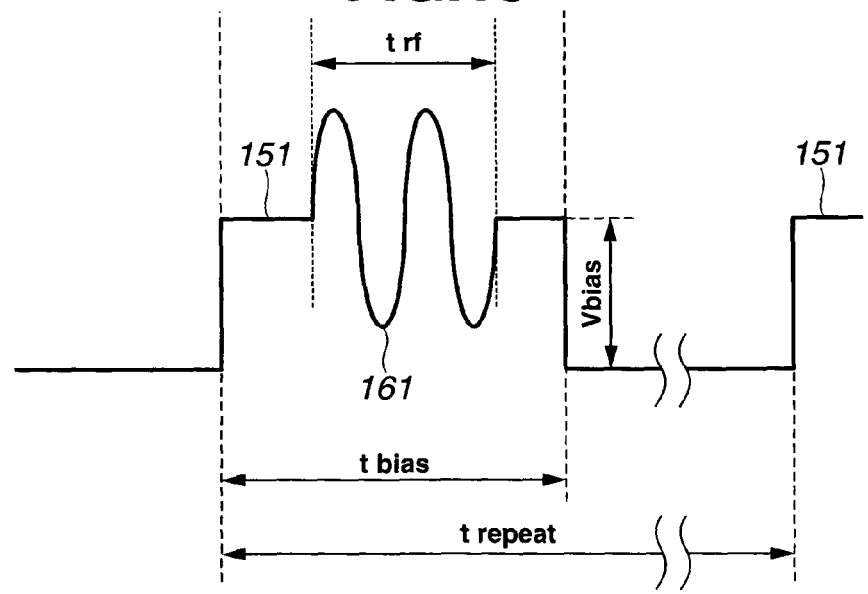
FIG. 13 shows a waveform of the c-MUT drive signal according to the third embodiment of the present invention.

FIG. 13 shows a waveform example of the ultrasonic transducer drive signal during transmission according to the third embodiment of the present invention. The means for supplying a DC bias voltage has a DC bias component "Vbias" with a predetermined amplitude at a predetermined period "trepeat" to reduce the effective voltage of the DC bias and generates a DC pulse signal 151 having a predetermined pulse width "tbias" as the DC bias amplitude. It also superimposes an original RF pulse signal 161 within the pulse width period of this DC pulse signal 151. Reference character "trf" denotes a RF pulse signal period superimposed within the pulse width tbias of the DC pulse signal. In this way, during transmission, the DC pulse signal 151 of a predetermined period having the DC bias component Vbias is superimposed on the RF pulse signal 161, a drive pulse signal is thereby generated, applied to the c-MUT, an ultrasound wave is thereby generated and transmitted to the body tissue.

At this time, the means for supplying the DC bias voltage DC, that is, DC bias power supply means is provided with the function of outputting the DC pulse signal 151 having the DC bias voltage component Vbias at the predetermined period trepeat and also provided with the function of controlling the pulse generation timing, pulse width tbias and pulse voltage Vbias of the DC pulse signal 151.

As for the DC bias voltage required during reception, it is also possible to carry out reception by generating the DC bias component Vbias at the predetermined period trepeat as the DC pulse signal 151 having the pulse width tbias according to the timing of reception and applying it to the c-MUT. During reception, the RF pulse is not superimposed.

Figure 14:
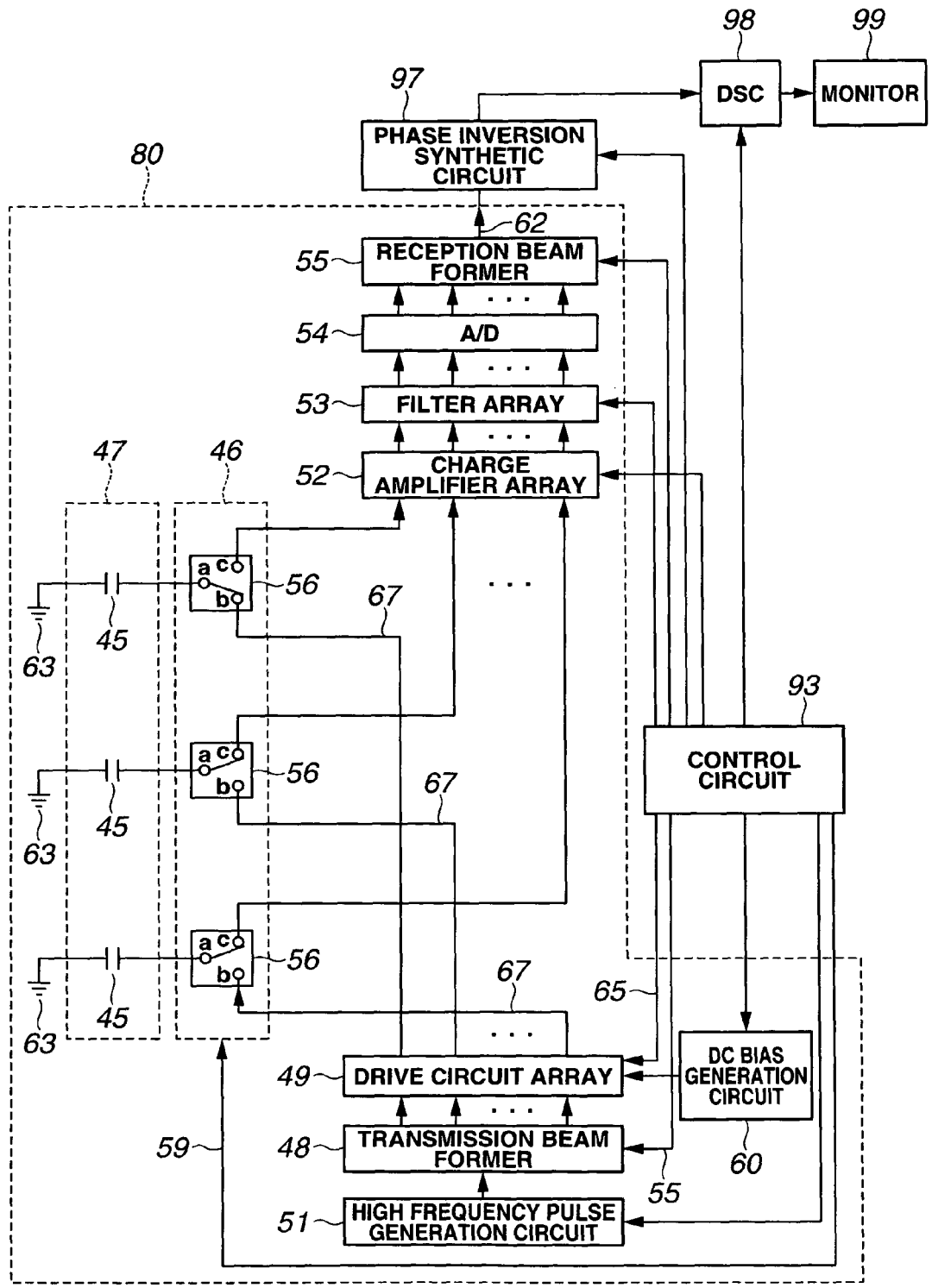
FIG. 14 is a block diagram showing the configuration of the ultrasonic probe apparatus using a c-MUT array according to the third embodiment of the present invention.

FIG. 14 shows a block diagram of an ultrasonic probe apparatus constructed using a transmission/reception dual-function type C-MUT array. FIG. 14 shows the configuration without the DC bias voltage on the receiving side. In this regard, the present applicant has experimentally confirmed that reception is possible even by eliminating the DC bias power supply for reception and without any DC bias voltage during reception about the c-MUT.

In FIG. 14, reference numeral 47 denotes a c-MUT array constructed by arranging a plurality of transmission/reception dual-function type c-MUT elements 45. As for each c-MUT element 45, one terminal is grounded, the other terminal is connected to a transducer terminal a of each transmission/reception switchover circuit 56 which constitutes a transmission/reception switchover switch array 46. The transmission/reception switchover circuit 56 is provided with the transducer terminal a connected to the c-MUT element 45, a transmitting side terminal b connected to the transmitting side circuit and a receiving side terminal c connected to the receiving side circuit. Reference numeral 63 denotes a ground (GND).

The c-MUT element 45 is, for example, a radial scan array type transducer which performs scanning with an ultrasonic beam around the insertion axis in the body cavity. The plurality of transmission/reception switchover circuits 56 which make up the transmission/reception switchover switch array 46 switch between transmission and reception according to a transmission/reception switching control signal 59.

Reference numeral 48 denotes a transmission beam former, 49 denotes a drive circuit array made up of a plurality of drive signal generators arranged, 50 denotes a DC bias generation circuit for transmission which is means for supplying a DC bias voltage and 51 denotes a RF pulse generation circuit.

The RF pulse generation circuit 51 has the function of generating a RF pulse signal having a low amplitude level equal to or less than 10 V. This RF pulse signal has a frequency of 1 kHz to 10 kHz and is generated with information on a frequency, pulse width and repeat time based on the control by a control circuit 93 composed of a processor and the like.

The transmission beam former 48 is constructed of a plurality of delay circuits corresponding to the plurality of c-MUT elements 45 respectively making up the c-MUT array 47, receives a RF pulse signal from the RF pulse generation circuit 51, generates a RF pulse signal having a time difference, that is, a delay time for each of the plurality of delay circuits under the control of the above described control circuit 93 based on the RF pulse signal and outputs them to each channel corresponding to each transducer element.

The transmission beam former 48 sets a delay time for each ultrasonic transducer element and this delay time setting makes it possible to scan the focus position in a sector shape or change the focus position in a far-to-near direction.

The DC bias generation circuit 50 has the function of generating a DC pulse signal provided with a predetermined pulse width having a low voltage level equal to or less than 10 V at a predetermined period. The DC bias generation circuit 50 generates a DC bias signal, that is, a DC pulse signal at delay timing that matches delay timing of each RF pulse signal output from each delay circuit which makes up the transmission beam former 48 based on the control by the control circuit 93 and supplies the signal to the drive circuit array 49. That is, a plurality of output lines (not shown) corresponding to the plurality of drive signal generation circuits which correspond in number to the transducer elements which constitute the drive circuit array 49 are drawn out of the DC bias generation circuit 50, and delay DC pulse signals that match the delay timings of the transmission RF pulse signals are sequentially generated and supplied to the plurality of drive signal generation circuits.

Each drive circuit array 49 is constructed of a plurality of drive signal generation circuits, each drive signal generation circuit adds up a low voltage DC pulse signal having a delay that matches each channel from the DC bias generation circuit 50 and a low voltage RF pulse signal output from each delay circuit of the transmission beam former 48, generates a low voltage drive pulse signal, and then amplifies the drive pulse signal to generate 150 V to 200 V high voltage drive pulse signals for driving the ultrasonic transducer elements and supplies them to the transmitting side terminal b of each transmission/reception switchover circuit 56 of the transmission/reception switchover switch array 46.

Each transmission/reception switchover circuit 56 of the transmission/reception switchover switch array 46 is provided with the transmitting side terminal b which inputs a drive pulse signal from each drive signal generation circuit of the drive circuit array 49 during transmission, the receiving side terminal c which outputs a pulse echo signal from each c-MUT element 45 of the c-MUT array 47 during reception and the common terminal a for inputting or outputting a signal to/from each c-MUT element 45 of the c-MUT array 47 when switched to the transmitting side terminal b or the receiving side terminal c during transmission or reception.

The plurality of transmission/reception switchover circuits 56 making up the transmission/reception switchover switch array 46 have a one-to-one correspondence with the plurality of c-MUT elements 45 making up the c-MUT array 47. At respective transmission timings, the plurality of transmission/reception switchover circuits 56 send the above described high voltage drive pulse signals of for driving the ultrasonic transducer elements to the corresponding c-MUT elements 45 and generate ultrasound waves.

In response to the ultrasound wave transmitted from each c-MUT element 45 of the c-MUT array 47, an echo signal is returned from the body tissue. The echo signal is received by each ultrasonic transducer element 45 of the ultrasonic transducer array 47 according to the reception timing and sent to each charge amplifier making up a charge amplifier array 52 and preamplified.

This charge amplifier array 52 has the impedance conversion function of realizing impedance-matching between the high impedance c-MUT element 45 before the charge amplifier and the low impedance circuit system after the charge amplifier and the amplification function of amplifying the voltage of a minute signal from the c-MUT element 45. That is, the c-MUT element 45 has very high output impedance, and therefore the transducer element echo output signal is sent to each charge amplifier of the charge amplifier array 52 which operates as a preamplifier having high input impedance and amplified. Furthermore, the ultrasonic signal which returns as an echo signal is very feeble and the output echo signal from the c-MUT element 45 is also as small as 0.5 V to 0.0051 when converted to a voltage and the voltage thereof needs to be amplified, for example, 100 to 1000 times.

The output signal of the charge amplifier array 52 is sent to a filter array 53 where various noise components including high frequency noise are removed, then sent to an A/D converter 54, converted to a digital signal and sent to a reception beam former 55 in the next stage. The reception beam former 55 is made up of a digital beam former which performs digital beam forming.

In FIG. 14, since the c-MUT array 47 in which the plurality of c-MUT elements 45 are arranged is used, many ultrasonic transducer elements 45 can receive individual echo signals and the reception beam former 55 is used to put together those many reception echo signals.

As for beam forming, the transmission beam former 48 also exists on the transmitting side and when a delay time is controlled appropriately by a delay time control signal, it is possible to determine the focal length of an ultrasound wave in the body tissue which corresponds to the delay time.

The reception beam former 55 is made up of a plurality of delay circuits which correspond to the plurality of c-MUT elements 45 making up the c-MUT array 47 and sets a delay time for each transducer element and this delay time setting allows an ultrasound wave to be received from a target focal length.

Each transducer element of the reception beam former 55 receives an ultrasound wave from the target focal length and the respective delay circuits then match their phases and then put them together.

When subjected to beam forming at the reception beam former 55, the ultrasound waves are transformed into a unified beam and output as a reception signal 42.

The reception signal 42 from the reception beam former 55 is input to a phase inversion synthetic circuit 97 as a harmonic signal processing circuit. The phase inversion synthetic circuit 97 extracts a second-order harmonic signal in the reception signal using a second-order harmonic extraction technology which will be explained in FIG. 16 later and generates a signal for a harmonic imaging diagnosis.

An ultrasonic pulse signal transmitted to the body tissue from the c-MUT element 45 is a signal which only includes a fundamental wave of a frequency f0, but when the fundamental wave f0 propagates in the body tissue, harmonics are generated due to nonlinearity of the body tissue. These harmonics enter the echo signal which is a reflected signal and are returned and received by the c-MUT elements 45. The phase inversion synthetic circuit 97 extracts a second-order harmonic signal from the reflected echo signal.

A digital scan converter 98 then converts the signal to an image using a signal for a harmonic imaging diagnosis and displays it on a monitor 99, and can thereby perform an ultrasonic diagnosis.

The control circuit 93 controls generation of RF pulse at the RF pulse generation circuit 51, performs delay control of the DC bias generation circuit 50, transmission beam former 48 and reception beam former 55, controls the drive circuit array 49, the charge amplifier array 52, the filter array 53, the phase inversion synthetic circuit 97 and the digital scan converter 98, and further controls the selection of the transducer elements for transmission and transducer elements for reception at the plurality of transmission/reception switchover circuits 56 making up the transmission/reception switchover switch array 46 by the transmission/reception switching control signal 59.

Next, the operation of the c-MUT array in FIG. 14 will be explained with reference to FIG. 15.

Figure 15:
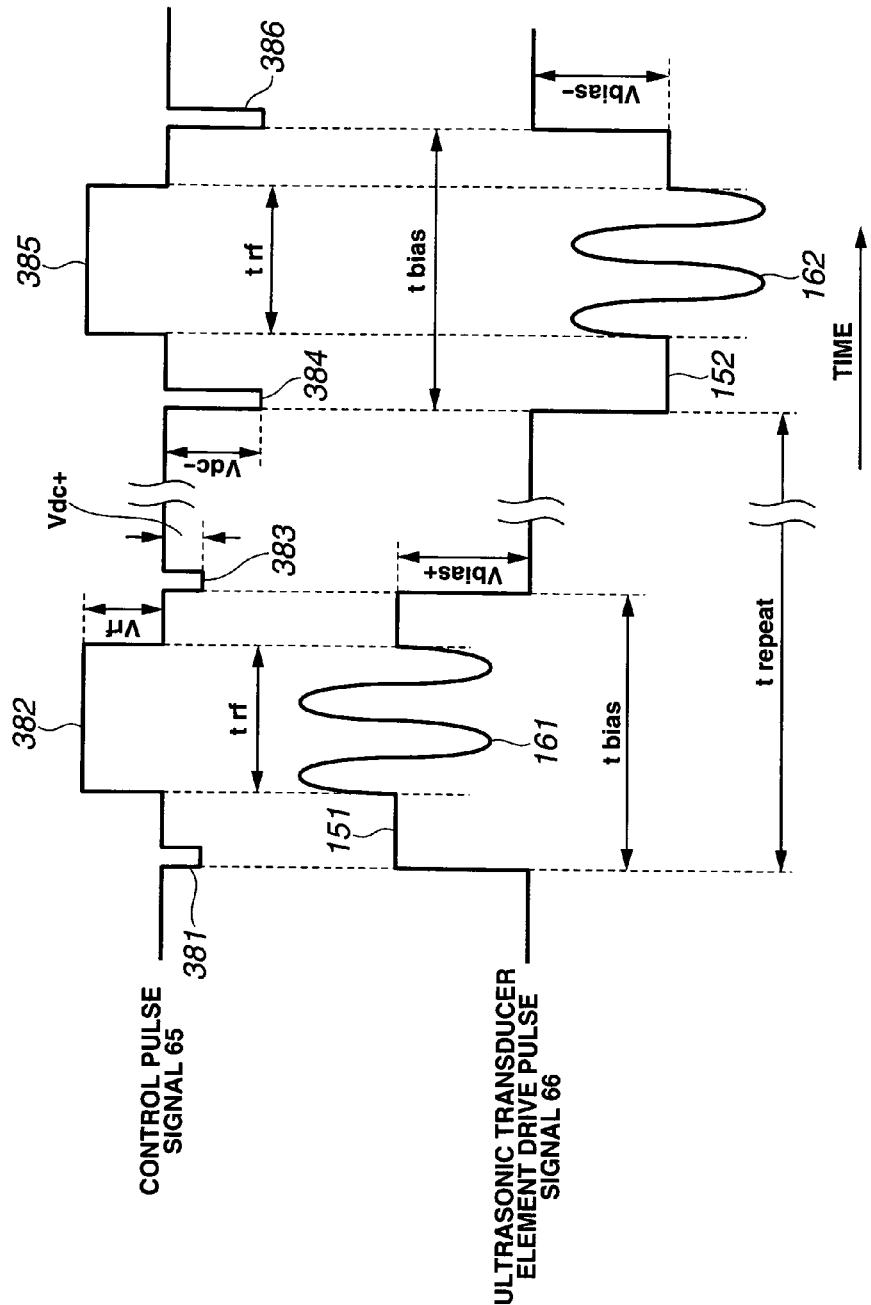
FIG. 15 is a waveform diagram of a control pulse signal and c-MUT element drive signal illustrating the operation of FIG. 14.

The upper part of FIG. 15 shows the waveform of a control pulse signal 65 which is generated at the control circuit 93 to control the drive circuit array 49. The lower part of FIG. 15 shows the waveform of a low voltage ultrasonic transducer element drive pulse signal 66 which is generated at each drive signal generation circuit of the drive circuit array 49.

Under the control of the control pulse signal 65 in the upper part of FIG. 15, each drive signal generation circuit of the drive circuit array 49 adds up the low voltage DC pulse signal with a delay corresponding to each transmission channel from the DC bias generation circuit 50 and the low voltage RF pulse signal output from each delay circuit of the transmission beam former 48, generates a low voltage drive pulse signal 66 shown in the lower part of FIG. 15, amplifies the drive pulse signal 66, generates a drive pulse signal 67 for driving the high voltage ultrasonic transducer element and supplies it to the transmitting side terminal b of each transmission/reception switchover circuit 56 of the transmission/reception switchover switch array 46.

In the upper part of FIG. 15, reference numeral 381 denotes a +DC bias start-up timing pulse, 382 denotes a high frequency signal generation timing pulse, 383 denotes a +DC bias stop timing pulse, 384 denotes a −DC bias start-up timing pulse, 385 denotes a high frequency signal generation timing pulse, 386 denotes a −DC bias stop timing pulse, Vrf denotes a RF pulse signal voltage to specify a RF pulse signal generation period trf, Vdc+ denotes a +DC bias start-up/stop pulse voltage and Vdc− denotes a −DC bias start-up/stop pulse voltage.

In the lower part of FIG. 15, reference numeral 151 denotes a +DC pulse signal, 152 denotes a −DC pulse signal, 161 and 162 denote RF pulse signals, trf denotes a RF pulse signal generation period, tbias denotes a DC bias signal generation period, Vdc+ denotes a +DC bias start-up/stop pulse voltage, Vdc− denotes a −DC bias start-up/stop pulse voltage, Vbias+ denotes a +DC bias voltage and Vbias− denotes a −DC bias voltage.

The pulse width trf of the positive voltage pulses 382 and 385 of the control pulse signal 65 shown in the upper part of FIG. 15 specifies the period during which RF pulse signals 161 and 162 in the lower part of FIG. 15 are being output. The negative voltage pulses 381 and 383 in the upper part of FIG. 15 specify timings of starting and stopping application of the positive DC bias voltage Vbias+ in the lower part of FIG. 15, the negative voltage pulses 384 and 386 in the upper part of FIG. 15 specify timing of starting and stopping application of the negative DC bias voltage Vbias− in the lower part of FIG. 15 and these negative voltage pulses 381, 383, 384 and 386 have polarities opposite to those of the pulses 382 and 385 which corresponded to the high frequency signal output periods. Furthermore, the difference (Vdc+ and Vdc−) in the magnitude of the voltage value in the upper part of FIG. 15 specifies the difference in the polarity between the DC bias voltages Vbias+ and Vbias− shown in the lower part of FIG. 15.

When driven by the signal waveform in the lower part of FIG. 15, an ultrasonic signal of an inverted phase is transmitted. When watching the first peak of the pulse, the first peak of the preceding pulse is Vbias++Vop (=maximum value of amplitude) and that of the following pulse is Vbias−+Vop (=minimum value of amplitude) and the phase is inverted. Here, Vop denotes the amplitude of the RF pulse signals 161 and 162.

Each drive signal generation circuit of the drive circuit array 49 has the function of generating a drive pulse signal 66 with the RF pulse signals 161 and 162 superimposed on the DC pulse signals 151 and 152, generates a double pulse signal which combines a first superimposed pulse signal composed of the RF pulse signal 161 superimposed on the DC pulse signal 151 having one polarity, for example, positive polarity and a second superimposed pulse signal with the RF pulse signal 162 having the same amplitude, frequency and polarity and the same shape as those of the RF pulse signal 161 used to form the first superimposed pulse signal superimposed on the DC pulse signal 152 having a polarity opposite to the polarity of the DC pulse signal used to form the first superimposed pulse signal, for example, negative polarity, in such a way that the two signals appear one after another with a predetermined time interval and outputs them as the ultrasonic transducer element drive pulse signal 66.

Figure 16:
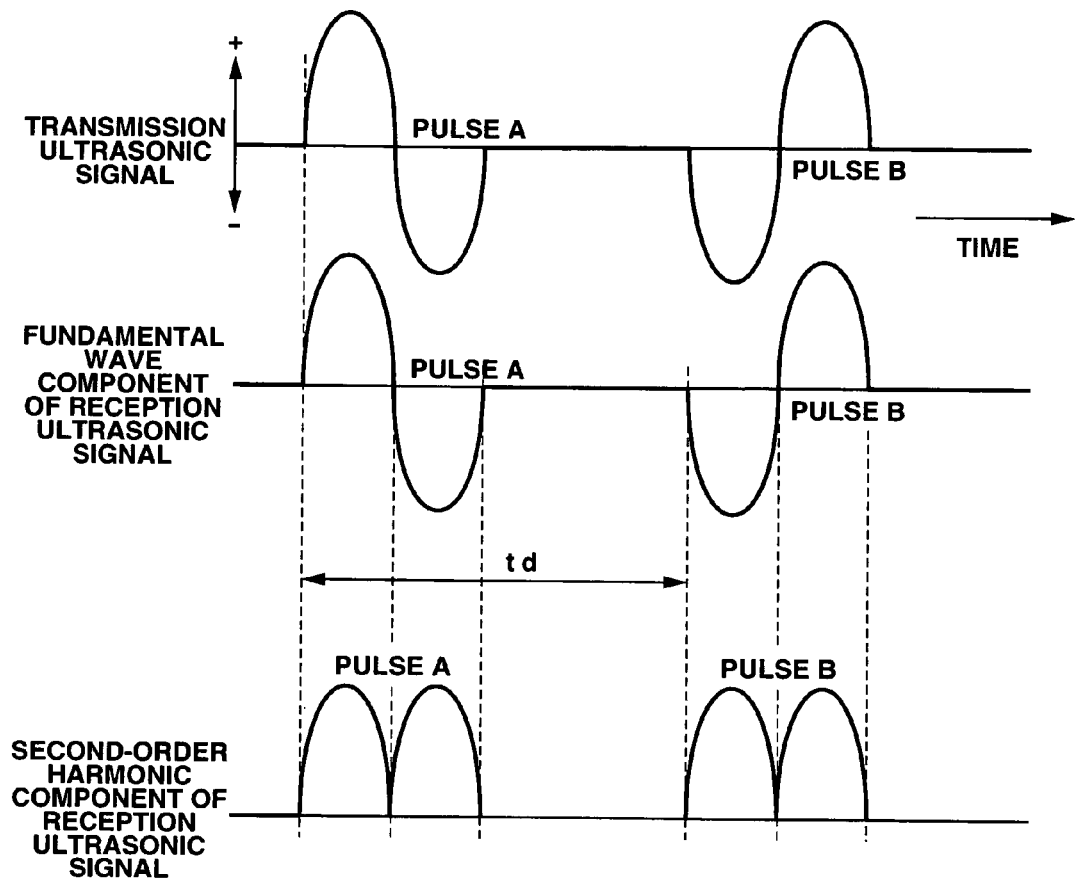
FIG. 16 is a waveform diagram illustrating a harmonic extraction technology.

When the ultrasonic transducer element drive pulse signal 66 which has a double pulse signal waveform as shown in the lower part of FIG. 15 is applied from each drive signal generation circuit of the drive circuit array 49 to each ultrasonic transducer element 45 through each transmission/reception switchover circuit 56, as for the ultrasonic signal output from each ultrasonic transducer element 45, an ultrasonic signal which corresponds to the first RF pulse signal and an ultrasonic signal which corresponds to the following RF pulse signal of the above described double pulse signal have mutually opposite phases such as pulses A and B illustrated in the upper part of FIG. 16 when modeled with two waves. When such a double-pulse signal combining pulses with inverted phases is transmitted to the body tissue, harmonics superimpose on a fundamental wave ultrasound wave influenced by nonlinearity of the body tissue. In this case, the response of the fundamental wave is first-order, that is, first power, and that of the second-order harmonic is a square. The "square" means that a negative component also becomes positive. Since the fundamental wave is the first power, positive remains positive and negative remains negative. Therefore, the fundamental wave of the ultrasonic signal which is received at each ultrasonic transducer element 45 is similar to the transmission ultrasonic signal in the upper part of FIG. 16 as shown in the middle row of FIG. 16, but the second-order harmonic component of the reception ultrasonic signal has only positive components as shown in the lower part of FIG. 16.

Therefore, when the receiving side circuit system reduces to 0 the time difference "td" between pulse A and pulse B which make up the double pulse in the reception ultrasonic signal and calculates the sum of the two, the fundamental wave component is eliminated with the addition of the positive component and the negative component, while the second-order harmonic component doubles with the addition of the positive component and the positive component. In other words, only the second-order harmonic component can be extracted. This is the harmonic component extraction technology of the harmonic imaging technology for a c-MUT. Using such a harmonic component extraction technology, the harmonic component which has a small sound pressure of 10 to 20 dB with respect to the sound pressure of the fundamental wave component can be separated and extracted from a reception signal in which both components are mixed.

For example, as means for reducing the time difference td to 0, the above described phase inversion synthetic circuit 97 temporarily saves the first pulse A in a memory and calculates the sum when the following pulse B arrives. In this way, when a double pulse which combines a pair of pulses of opposite phases is applied to a body tissue, the response of the fundamental wave (to be exact, all odd-orders) is the first-order, that is, first power and that of the second-order harmonic (to be exact, all even-orders) has no negative signals, and therefore when both pulses are added up with their respective phase equalized, the fundamental wave (to be exact, all odd-orders) is eliminated and only the second-order harmonics (to be exact, all even-orders) remain.

In an actual ultrasonic diagnosis, not only harmonics but also a fundamental wave must be observed. The fundamental wave will be extracted using different means which is conventionally practiced. Eventually, both extracted images are added up to construct an ultrasonic image.

The DC pulse signals which are the DC bias signals shown in FIG. 13 or FIG. 15 have substantially vertical pulse rising and falling edges. Applying or stopping to apply such a precipitously high DC bias voltage (approximately 100 V) to the ultrasonic transducer may cause the capacitative transducer to easily deteriorate and shorten the life as the transducer.

On the other hand, as for the RF pulse signal shown in FIG. 13 or FIG. 15, when the high frequency component of a signal increases, there is a possibility that the load on the drive signal generation circuit may increase.

Therefore, remedial actions for these problems will be explained with reference to FIG. 17 and FIG. 18 below.

Figure 17:
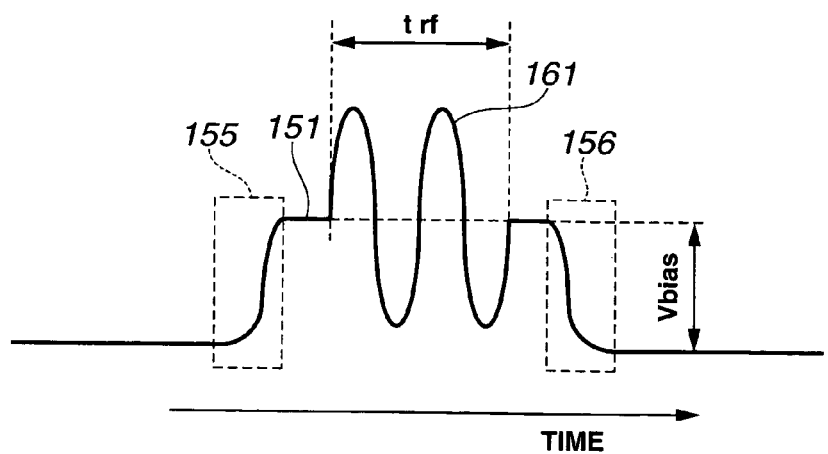
FIG. 17 is a waveform diagram showing a modification example of the c-MUT element drive signal.

FIG. 17 shows a modification example of the waveform of a c-MUT element drive signal. Blunting a rising edge 155 and a falling edge 156 of a DC pulse signal 151 and transforming them into gentle inclinations prevents a precipitously high voltage from applying to the ultrasonic transducers. Vbias denotes a DC bias component and trf denotes a RF pulse signal period.

Figure 18:
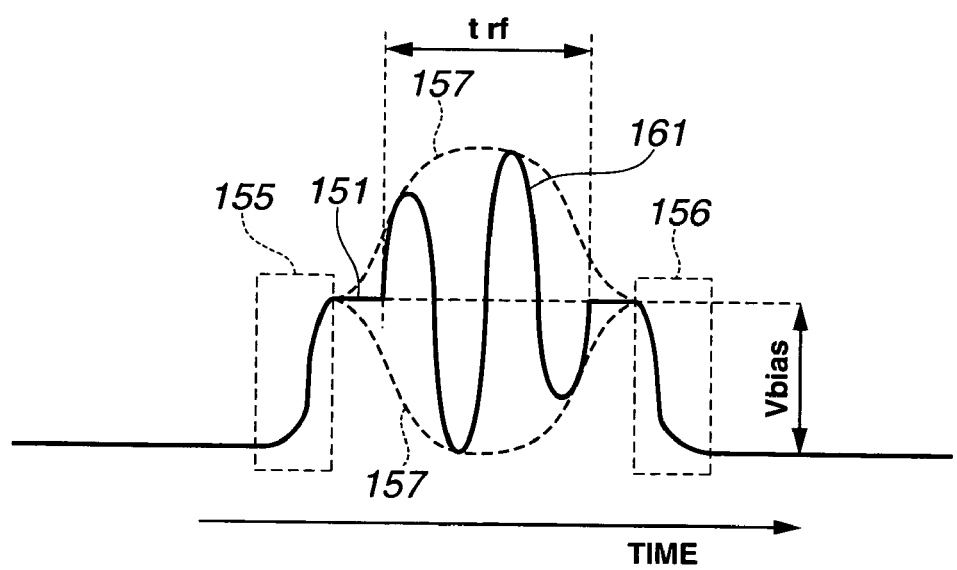
FIG. 18 is waveform diagram showing another modification example of the c-MUT element drive signal.

FIG. 18 shows another modification example of the waveform of a c-MUT element drive signal. In addition to trans-forming the rising edge 155 and the falling edge 156 into gentle inclinations as in FIG. 17, a RF pulse signal 161 is formed into a burst wave multiplied by a window function 157. As the window function 157, any one of Gaussian, Hamming, Hanning and Blackman functions may be used.

Applying the window function eliminates the high frequency component of the signal, reduces the load on high voltage output amplifier in the drive signal generator and reduces the load on the drive signal generator (pulsar). Furthermore, it is possible to suppress the occurrence of a time axis side lobe, make the most of the original wideband characteristic of the c-MUT and obtain a high resolution ultrasonic diagnostic image.

As described above, the third embodiment of the present invention can realize an ultrasonic probe apparatus using a c-MUT operating on a low operating effective voltage, usable in the body cavity and applicable to a harmonic imaging diagnosis.

Fourth Embodiment

FIG. 19 shows a block diagram showing the configuration of an ultrasonic diagnostic apparatus according to a fourth embodiment of the present invention. This fourth embodiment is constructed of an ultrasonic probe apparatus 80 using the ultrasonic transducer array in FIG. 14 in the third embodiment and a main apparatus 90 which processes an output signal from the ultrasonic probe apparatus, generates an ultrasonic image signal and displays it on a display device. The outside of the ultrasonic probe apparatus 80 is covered with a protection sheath.

The ultrasonic probe apparatus 80 is constructed of a plurality of c-MUT elements 45 assembled on a silicon substrate using, for example, a micromachining technology, drive control means constructed substantially integral therewith and signal transmitting means for exchanging signals. The c-MUT elements 45 are, for example, radial scan array type transducers which perform scanning with an ultrasonic beam around an insertion axis in the body cavity.

The ultrasonic probe apparatus 80 is provided with an ultrasonic transducer array 47 made up of the plurality of c-MUT elements 45, a transmission/reception processing section 91 as drive control means for performing transmission processing on an ultrasonic drive signal for each c-MUT element 45 of the ultrasonic transducer array 47 or performing reception processing on an echo signal output from each c-MUT element 45 and a selector 92 as signal transmitting means for transmitting a pulse signal to a predetermined instructed ultrasonic transducer element 45 based on an operation instruction signal of a CPU 93 in the main apparatus 90.

The transmission/reception processing section 91 is at least provided with a transmission delay circuit 131, a bias signal application circuit 132, a drive signal generation circuit 133, a transmission/reception switchover circuit 134, a preamplifier 135 and a beam former 136.

The main apparatus 90 processes an output signal from the ultrasonic probe apparatus 80, constructs an image signal and displays an ultrasonic diagnostic image of the interior of the body cavity on a monitor which is a display device.

The main apparatus 90 is provided with the CPU 93, a trigger signal generation circuit 94, an echo signal processing, circuit 95, a Doppler signal processing circuit 96, a harmonic signal processing circuit 97 and an ultrasonic image processing section 98.

The CPU 93 outputs operation instruction signals to various circuits and processing sections provided for this ultrasonic diagnostic apparatus, receives feedback signals from the various circuits and processing sections and carries out various types of control.

The trigger signal generation circuit 94 outputs repeat pulse signals which are transmission and reception timing signals when driving each ultrasonic transducer element 45.

The echo signal processing circuit 95 generates B mode image data which is a visible image based on a received beam signal which is an ultrasound wave output from each ultrasonic transducer element 45 and then reflected on an organ in a body and a boundary thereof or the like, returned to and received by the ultrasonic transducer element 45.

The Doppler signal processing circuit 96 extracts a mobile component of a tissue, that is, a blood flow component from the received beam signal output from the ultrasonic transducer element 45 using a Doppler effect and generates color data to color the positions of the blood flow in an ultrasonic tomogram.

The above described harmonic signal processing circuit 97 has the same function as that of the phase inversion synthetic circuit 97 (FIG. 14), uses a filter whose central frequency is a second-order harmonic frequency (or a third-order harmonic frequency) to extract a signal of that frequency component from the received beam signal output from each ultrasonic transducer element 45, amplifies the signal and generates image data for a harmonic imaging diagnosis.

The above described ultrasonic image processing section 98 is constructed of, for example, a digital scan converter and constructs a B mode image, Doppler image, harmonic imaging image or the like based on image data generated by, for example, the echo signal processing circuit 95, Doppler signal processing circuit 96 and harmonic signal processing circuit 97 or the like, respectively. At the same time, the ultrasonic image processing section 98 also performs character overlay of characters or the like through the CPU 93. It is possible to output the video signal built by this ultrasonic image processing section 98 to a monitor 99 and display an ultrasonic tomogram which is one of observed images on the screen of the monitor 99.

The above described transmission delay circuit 131 determines timing at which a drive voltage is applied to each c-MUT element 45 and makes a setting so as to perform predetermined sector scanning or the like.

The above described bias signal application circuit 132 applies a predetermined bias signal to the above described drive signal generation circuit 133. Examples of this bias signal include one that uses the same DC voltage during both transmission and reception, one that sets a high voltage during transmission and changes it to a low voltage during reception or one that superimposes an AC component on a DC component to take, for example, a correlation.

The DC bias voltage is necessary to obtain an ultrasonic transmission waveform having the same waveform as the transmission voltage waveform during transmission. Note that the DC bias voltage is not always necessary during reception as described above.

The above described drive signal generation circuit 133 generates a burst wave which is a drive pulse signal corresponding to a desired ultrasound waveform based on the output signal from the above described transmission delay circuit 131.

The above described transmission/reception switchover circuit 134 switches one c-MUT element 45 between a transmission state and a reception state. In the transmission state, the transmission/reception switchover circuit 134 applies the above described drive pulse signal to the c-MUT element 45, while in the reception state, it receives the above described echo information and outputs a charge signal thereby generated between the electrodes of the c-MUT element 45 to the preamplifier 135.

The above described preamplifier 135 converts the charge signal output from the transmission/reception switchover circuit 134 to a voltage signal and amplifies it.

The above described beam former 136 outputs a received beam signal obtained by synthesizing each ultrasonic echo signal output from the above described preamplifier 135 with the same delay as that at the above described transmission delay circuit 131 or a different delay time.

It is possible to perform an ultrasonic observation using an ultrasound wave set to the above described focal length by giving a predetermined phase difference based on an operation instruction signal from the CPU 93, driving the respective c-MUT elements 45, transmitting an ultrasound wave set to a predetermined focal length from the scanning plane of the ultrasound wave of the c-MUT array 47, adding a delay similar to the delay at the transmission delay circuit 131 and synthesizing the signals using the above described beam former 136 and outputting it as the received beam signal.

The fourth embodiment of the present invention can realize an ultrasonic diagnostic apparatus using c-MUTs operating with a low operating effective voltage, usable in the body cavity and also applicable to a harmonic imaging diagnosis.

It goes without saying that the present invention is applicable not only to an ultrasonic probe apparatus and an ultrasonic diagnostic apparatus using this but also to an ultrasonic endoscopic diagnostic apparatus which simultaneously obtains an endoscopic image and an ultrasonic image by combining an electronic endoscopic apparatus and an ultrasonic diagnostic apparatus.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic probe apparatus comprising:
   a capacitive micromachined ultrasonic transducer (c-MUT) for transmitting and receiving ultrasound waves, the c-MUT comprising a plurality of transducer elements arranged in an array structure;
   a transmission control portion comprising:
      a transmission transducer elements selecting section adapted to select transmission transducer elements for transmitting the ultrasound wave from the plurality of transducer elements,
      a driving section adapted to apply a drive signal to the selected transmission transducer elements, the drive signal an RF pulse signal with DC bias signal superimposed thereon,
      a transmission delay section adapted to perform scanning with a transmission ultrasonic beam, and
      a bias adjustment section adapted to adjust a voltage value of the DC bias signal; and
   a reception control portion comprising:
      a reception transducer elements selecting section adapted to select reception transducer elements for receiving ultrasound waves as a plurality of reception signals from the plurality of transducer elements,
      an amplification section adapted to amplify the plurality of reception signals,
      a frequency band pass filtering processing section having a plurality of different frequency band pass filtering characteristics including at least those for a low pass filtering and a high pass filtering, the frequency band pass filtering processing section being adapted to select any one of the frequency band pass filtering characteristics and to perform frequency band pass filtering of the plurality of reception signals based on the selected frequency band pass filtering characteristic, an analog/digital signal conversion section adapted to convert the plurality of reception signals which have passed through the frequency band pass filtering processing section to a plurality of digital signals, a beam synthesizing section adapted to synthesize the plurality of digital signals to a single signal, an image constructing section adapted to convert the single signal to an image, and an image display section for displaying the image.

2. The ultrasonic probe apparatus according to claim 1, wherein the plurality of different frequency band pass filtering characteristics are three frequency band pass filtering characteristics of a low frequency band pass filtering characteristic, a high frequency band pass filtering characteristic and an intermediate frequency band pass filtering characteristic which is intermediate between the low frequency band pass filtering characteristic and the high frequency band pass filtering characteristic.

3. The ultrasonic probe apparatus according to claim 1, further comprising a section for controlling a voltage setting of the bias adjustment section in conjunction with a frequency band pass filtering characteristic selection of the frequency band pass filtering processing section.

4. The ultrasonic probe apparatus according to claim 3, wherein the frequency band pass filtering processing section is set to a low frequency band pass filtering characteristic when the DC bias voltage is set to be low and the frequency band pass filtering processing section is set to a high frequency band pass filtering characteristic when the DC bias voltage is set to be high.

5. The ultrasonic probe apparatus according to claim 1, wherein the drive signal from the drive section is a pulse signal composed of a DC pulse signal superimposed on a RF pulse signal.

6. The ultrasonic probe apparatus according to claim 5, wherein the DC pulse signal draws a curve similar to a Gaussian function or a COS function on a rising edge and a falling edge.

7. The ultrasonic probe apparatus according to claim 5, wherein the RF pulse signal is a spike-shaped pulse.

8. The ultrasonic probe apparatus according to claim 1, wherein the voltage setting of the bias adjustment section and the selection of the frequency band pass filtering processing section are successively changed, ultrasonic reception data obtained for each change is temporarily stored in a storage section, the data are synthesized and an image constructing section constructs an ultrasonic diagnostic image signal.

9. The ultrasonic probe apparatus according to claim 8, wherein in the voltage setting of the bias adjustment section, the frequency band pass filtering processing section selects a low frequency band pass filtering characteristic when selecting a low voltage setting and the frequency band pass filtering processing section selects a high frequency band pass filtering characteristic when setting a high voltage.

10. The ultrasonic probe apparatus according to claim 1, wherein in the voltage setting of the bias adjustment section, the transmission transducer elements selecting section selects a transmission transducer element disposed in the vicinity of the periphery of an ultrasonic transmission opening when selecting a low voltage setting and the transmission transducer elements selecting section selects a transmission transducer element disposed in the vicinity of a central part of the ultrasonic transmission opening when selecting a high voltage setting.

11. An ultrasonic probe apparatus comprising:
means for supplying a DC bias voltage;
drive signal generation means for generating a drive signal with the DC bias voltage superimposed on an RF pulse signal; and
a capacitive micromachined ultrasonic transducer (c-MUT) for transmitting and receiving ultrasound waves by being applied with the drive signal, wherein
the means for supplying the DC bias voltage is adapted to output a DC pulse signal at a predetermined period and controlling pulse generation timing, pulse width and pulse voltage of the DC pulse signal, and
the drive signal generation means generates a double pulse signal combining a first superimposed pulse signal composed of an RF pulse signal superimposed on an DC pulse signal with one polarity and a second superimposed pulse signal composed of an RF pulse signal having the same shape as that of the RF pulse signal used to form the first superimposed pulse signal superimposed on an DC pulse signal having a polarity opposite to the polarity of the DC pulse signal used to form the first superimposed pulse signal in such a way that the two signals appear one after another with a predetermined time interval.

12. The ultrasonic probe apparatus according to claim 11, wherein the drive signal generation means comprises means for performing control in such a way that the RF pulse signal is located within the pulse width of the DC pulse signal.

13. The ultrasonic probe apparatus according to claim 12, further comprising means for switching a polarity of the DC pulse signal by an instruction signal from outside.

14. The ultrasonic probe apparatus according to claim 12, further comprising control means for reducing the voltage of the DC pulse signal to zero by an instruction signal from outside.

15. The ultrasonic probe apparatus according to claim 11, further comprising:
a c-MUT assembled using a micromachine technology;
drive control means constructed substantially integral therewith; and
signal transmission means for exchanging signals.

16. The ultrasonic probe apparatus according to claim 15, wherein the c-MUT is a radial scanning array type transducer which performs scanning with an ultrasonic beam around an insertion axis in a body cavity.

17. The ultrasonic probe apparatus according to claim 15, wherein the ultrasonic probe apparatus is covered with a protection sheath.

18. The ultrasonic probe apparatus according to claim 11, wherein the DC pulse signal has a gentle inclination on the rising edge and/or the falling edge.

19. The ultrasonic probe apparatus according to claim 11, wherein the RF pulse signal is a burst wave multiplied by a window function.

20. An ultrasonic diagnostic apparatus, comprising:
the ultrasonic probe apparatus according to claim 15 or 16; and
a main apparatus which processes an output signal from the ultrasonic probe apparatus, constructs an image signal and displays an ultrasonic diagnostic image of the interior of the body cavity.

* * * * *